(12) United States Patent
Flohr et al.

(10) Patent No.: US 6,620,811 B2
(45) Date of Patent: Sep. 16, 2003

(54) ISONICOTIN- AND NICOTINAMIDE DERIVATIVES OF BENZOTHIAZOLES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/288,100

(22) Filed: Nov. 5, 2002

(65) Prior Publication Data

US 2003/0134854 A1 Jul. 17, 2003

(30) Foreign Application Priority Data

Nov. 19, 2001 (EP) ............................................ 01127312

(51) Int. Cl.[7] ..................... A61K 31/5377; A61P 25/28; C07D 413/14
(52) U.S. Cl. ................... 514/233.8; 544/58.2; 544/121; 544/130; 544/131; 544/364; 546/193; 546/270.1
(58) Field of Search ................................ 544/131, 130; 546/270.1; 514/233.8

(56) References Cited

U.S. PATENT DOCUMENTS 6,521,754 B2 * 2/2003 Alanine et al. ............. 544/129

FOREIGN PATENT DOCUMENTS

| EP | 113219 | 7/1984 |
| EP | 0 295656 | 12/1988 |
| WO | WO 0197786 | 12/2001 |

OTHER PUBLICATIONS

Alanine et al, Chem Abstracts, vol. 136, No. 69803, 2001.*
Poulsen et al., Bioorganic & Medicinal Chemistry, 6, pp. 619–641 (1998).
Müller et al., Bioorganic & Medicinal Chemistry, 6, pp. 707–719 (1998).
Kim et al., J. Med. Chem., 41, pp. 2835–2845 (1998).
Li et al., J. Med. Chem., 41, pp. 3186–3201 (1998).
Baraldi et al., J. Med. Chem., 41, pp. 2126–2133 (1998).
Li et al., J. Med. Chem., 42, pp. 706–721 (1999).
Baraldi et al., J. Med. Chem., 39, pp. 1164–117 (1996).
Colotta et al., Arch. Pharm. Pharm. Med. Chem., 332, pp. 39–41 (1999).
Auchampach et al., Am. J. Physiol., 276, pp. H1113–1116 (1999).
Haas et al., Naunyn Schmiedeberg's Arch. Pharmacol., 362, pp. 375–381 (2000).
Dionisotti et al., Br. J. Pharmacol., 121, pp. 353–360 (1997).
Baraldi P.G., et al, Drug Development Research, New York, NY, vol. 46, No. 2, pp. 126–133 (1999).

* cited by examiner

Primary Examiner—Robert W. Ramsuer
(74) Attorney, Agent, or Firm—George W. Johnston; Patricia S. Rocha-Tramaloni; Lyman H. Smith

(57) ABSTRACT

The present invention relates to compounds of the formula

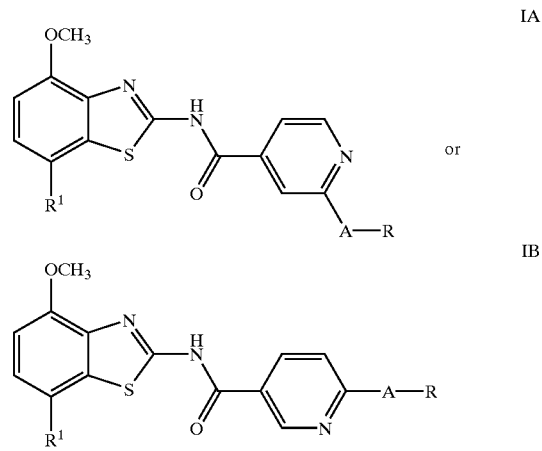

wherein R1, A and R are as described within. The compounds of the present invention have been found to be adenosine receptor ligands. Specifically, the compounds of the present invention have an affinity to the $A_{2A}$-receptor and are therefore useful in the treatment of diseases related to this receptor.

43 Claims, No Drawings

ISONICOTIN- AND NICOTINAMIDE DERIVATIVES OF BENZOTHIAZOLES

BACKGROUND OF THE INVENTION

The present invention generally relates to benzothiazole compounds useful as adenosine receptor ligands. Specifically, the present invention relates to compounds having good affinity to the $A_{2A}$-receptor and a high selectivity to the $A_1$- and $A_3$ receptors.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises CAMP as a second messenger. The $A_1$ and $A_3$ receptors, coupled with $G_i$ proteins inhibit adenylate cyclase, leading to a decrease in cellular CAMP levels, while $A_{2A}$ and $A_{2B}$ receptors couple to $G_s$ proteins and activate adenylate cyclase, leading to an increase in cellular CAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho)physiological conditions. Under conditions of increased demand and decreased availability of energy (such as hypoxia, hypoglycemia, and/or excessive neuronial activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2b}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting, at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating, influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treament of diabetes mellitus and obesity.

Numerous documents describe the current knowledge on adenosine receptors, for example the following publications:
Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

SUMMARY OF THE INVENTION

The present invention relates to compounds of the formula

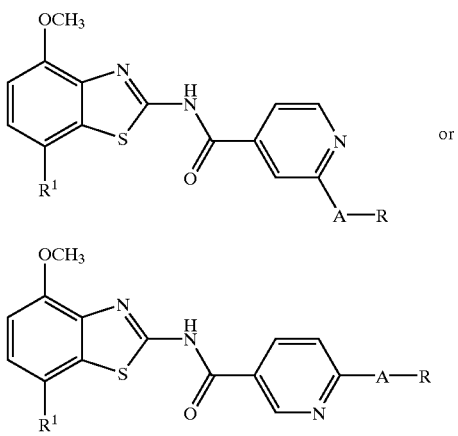

wherein $R^1$, A and R are as defined herewithin.

The present invention generally relates to compounds of formula IA and IB per se, the use of compounds of formula IA and IB and their pharmaceutically acceptable salts for the manufacture of medicaments for the treatment of diseases, related to the adenosine $A_2$ receptor. The present invention further relates to the manufacture of compounds of formula IA and IB, medicaments based on a compound in accordance with the invention and their production as well as the use of compounds of formula IA and IB in the control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The present invention relates to compounds of the formula

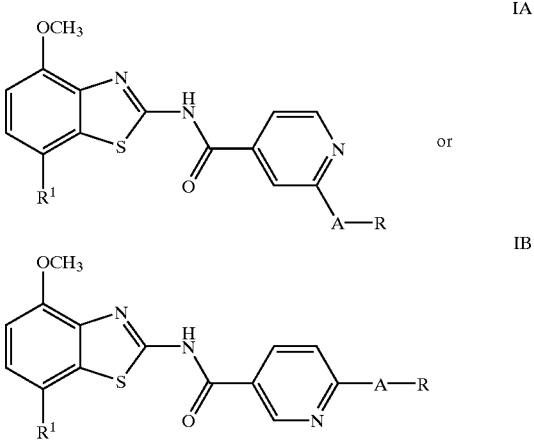

wherein
$R^1$ is phenyl, piperidin-1-yl or morpholinyl;
A is —O— and
R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl, —(CH$_2$)$_n$—N(R")$_2$, —(CH$_2$)$_n$-pyridinyl, —(CH$_2$)$_n$—CF$_3$, —(CH$_2$)$_n$-2-oxo-pyrrolidinyl or C$_{4-6}$-cycloalkyl;
R" is independently selected from hydrogen and lower alkyl; and
n is 1 or 2; or
A is —N(R')— and
R is lower alkyl, C$_{4-6}$-cycloalkyl, —(CH$_2$)$_n$—O-lower alkyl, —(CH$_2$)$_n$-pyridinyl, —(CH$_2$)$_n$-piperidinyl, —(CH$_2$)$_n$-phenyl, —(CH$_2$)$_n$—N(R")—C(O)-lower alkyl, —(CH$_2$)$_n$-morpholinyl, or —(CH$_2$)$_n$—N(R")$_2$;
R' and R" are independently selected from hydrogen and lower alkyl; and
n is 1 or 2; or
A is —CH$_2$— and
R is —N(R")—(CH$_2$)$_m$—O-lower alkyl, —N(R")$_2$, S-lower alkyl, or is acetidinyl, pyrrolidinyl or piperidinyl, which are optionally substituted by hydroxy or lower alkoxy or is morpholinyl, —N(R")—(CH$_2$)$_m$—C$_{4-6}$-cycloalkyl, —N(R")—(CH$_2$)$_m$—C(O) O-lower alkyl, —N(R")—(CH$_2$)$_m$—C(O)OH, -2-oxo-pyrrolidinyl, —N(R")—C(O)O-lower alkyl, —O(CH$_2$)$_m$—O-lower alkyl or alkoxy;
R" is independently selected from hydrogen and lower alkyl; and
m is 1, 2 or 3;
or
A is —S— and
R is lower alkyl;
or
A—R are together
-piperazinyl, substituted by lower alkyl, —C(O)-lower alkyl or an oxo group, or is piperidinyl, substituted by lower alkoxy or hydroxy, or is morpholinyl, substituted by lower alkyl, or is —C$_{4-6}$-cycloalkyl, -azetidin-1-yl, optionally substituted by hydroxy or lower alkoxy, thiomorpholine-1,1-dioxo, -tetrahydopyran or 2-oxa-5-aza-bicyclo[2.2.1]hept-5-yl;
and pharmaceutically acceptable acid addition salts thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group, containing 4–6 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulphonic acid and the like.

Preferred compound of the present application are compounds of formula IA, wherein $R^1$ is morpholinyl and A is —O—. Particularly preferred are those compounds, wherein R is cycloalkyl, —(CH$_2$)$_n$—NHC(O)CH$_3$, —(CH$_2$)$_n$—N(R")$_2$,—(CH$_2$)$_n$—O-lower alkyl or lower alkyl, for example the following compounds:

2-(2-methoxy-ethoxy)-N-(4-methoxy-7-morpholin-4-yl-benzothiazol-2-yl)-isonicotinamide, 2-ethoxy-N-(4-methoxy-7-morpholin-4-yl-benzothiazol-2-yl)-isonicotinamide, 2-methoxy-N-(4-methoxy-7-morpholin-4-yl-benzothiazol-2-yl)-isonicotinamide, 2-isopropoxy-N-(4-methoxy-7-morpholin-4-yl-benzothiazol-2-yl)-isonicotinamide, 2-cyclohexyloxy-N-(4-methoxy-7-morpholin-4-yl-benzothiazol-2-yl)-isonicotinamide, 2-cyclopentyloxy-N-(4-methoxy-7-morpholin-4-yl-benzothiazol-2-yl)-isonicotinamide, 2-(2-dimethylamino-ethoxy)-N-(4-methoxy-7-morpholin-4-yl-benzothiazol-2-yl)-isonicotinamide or 2-(2-acetylamino-ethoxy)-N-(4-methoxy-7-morpholin-4-yl-benzothiazol-2-yl)-isonicotinamide.

Further preferred are compounds of formula IA, wherein $R^1$ is morpholinyl, A is —O— and R is —(CH$_2$)$_n$-pyridinyl, —(CH$_2$)$_n$-morpholinyl or —(CH$_2$)$_n$-2-oxo-pyrrolidinyl, for example the following compounds:

2-benzyloxy-N-(4-methoxy-7-morpholin-4-yl-benzothiazol-2-yl)-isonicotinamide,

N-(4-methoxy-7-morpholin-4-yl-benzothiazol-2-yl)-2-(pyridin-2-ylmethoxy)-isonicotinamide, N-(4-methoxy-7-morpholin-4-yl-benzothiazol-2-yl)-2-[2-(2-oxo-pyrrolidin-1-yl)-ethoxy]-isonicotinamide or N-(4-methoxy-7-morpholin-4-yl-benzothiazol-2-yl)-2-(2-morpholin-4-yl-ethoxy)-isonicotinamide.

Further preferred are compounds of formula IA, wherein $R^1$ is morpholinyl, A is —NR'— and R is —(CH$_2$)$_n$-pyridinyl, —(CH$_2$)$_n$-piperidinyl, —(CH$_2$)$_n$-phenyl or —(CH$_2$)$_n$-morpholidinyl, for example the following compounds:

N-(4-methoxy-7-morpholin-4-yl-benzothiazol-2-yl)-2-[methyl-(2-pyridin-2-yl-ethyl)-amino]-isonicotinamide, N-(4-methoxy-7- morpholin-4-yl-benzothiazol-2-yl)-2-(2-pyridin-2-yl-ethylamino)-isonicotinamide, N-(4-methoxy-7-morpholin-4-yl-benzothiazol-2-yl)-2-1(pyridin-2-ylmethyl)-amino]-isonicotinamide, 2-[ethyl-(2-pyridin-2-yl-ethyl)-amino]-N-(4-methoxy-7-morpholin-4-yl-benzothiazol-2-yl)-isonicotinamide, N-(4-methoxy-7-morpholin-4-yl-benzothiazol-2-yl)-2-(2-morpholin-4-yl-ethylamino)-isonicotinamide, N-(4-methoxy-7-morpholin-4-yl-benzothiazol-2-yl)-2-[methyl-(2-piperidin-1-yl-ethyl)-amino]-isonicotinamide, N-(4-methoxy-7-morpholin-4-yl-benzothiazol-2-yl)-2-(2-piperidin-1-yl-ethylamino)-isonicotinamide, 2-benzylamino-N-(4-methoxy-7-morpholin-4-yl-benzothiazol-2-yl)-isonicotinamide, 2-(benzyl-methyl-amino)-N-(4-methoxy-7-morpholin-4-yl-benzothiazol-2-yl)-isonicotinamide, N-(4-methoxy-7-morpholin-4-yl-benzothiazol-2-yl)-2-(methyl-phenethyl-amino)-isonicotinamide or N-(4-methoxy-7-morpholin-4-yl-benzothiazol-2-yl)-2-phenethylamino-isonicotinamide.

Further preferred are compounds of formula IA, wherein $R^1$ is morpholinyl, A is —NR'— and R is lower alkyl, cycloalkyl, —(CH$_2$)$_n$—O-lower alkyl, —(CH$_2$)$_n$—N(R")$_2$ or —(CH$_2$)$_n$—NR"—C(O)-lower alkyl, for example the following, compounds:

2-[(2-methoxy-ethyl)-methyl-amino]-N-(4-methoxy-7-morpholin-4-yl-benzothiazol-2-yl)-isonicotinamide, 2-(2-methoxy-ethylamino)-N-(4-methoxy-7-morpholin-4-yl-benzothiazol-2-yl)-isonicotinamide, 2-[ethyl-(2-methoxy-ethyl)-amino]-N-(4-methoxy-7-morpholin-4-yl-benzothiazol-2-yl)-isonicotinamide, 2-(2-ethoxy-ethylamino)-N-(4-methoxy-7-morpholin-4-yl-benzothiazol-2-yl)-isonicotinamide, 2-(2-acetylamino-ethylamino)-N-(4-methoxy-7-morpholin-4-yl-benzothiazol-2-yl)-isonicotinamide, 2-cyclohexcylamino-N-(4-methoxy-7-morpholin-4-yl-benzothiazol-2-yl)-isonicotinamide, 2-cyclopentylamino-N-(4-methoxy-7-morpholin-4-yl-benzothiazol-2-yl)-isonicotinamide, 2-cyclobutylamino-N-(4-methoxy-7-morpholin-4-yl-benzothiazol-2-yl)-isonicotinamide, 2-(2-dimethylamino-ethylamino)-N-(4-methoxy-7-morpholin-4-yl-benzothiazol-2-yl)-isonicotinamide, N-(4-methoxy-7-morpholin-4-yl-benzothiazol-2-yl)-2-propylamino-isonicotinamide, N-(4-methoxy-7-morpholin-4-yl-benzothiazol-2-yl)-2-(methyl-propyl-amino)-isonicotinamide, 2-(cyclohexyl-methyl-amino)-N-(4-methoxy-7-morpholin-4-yl-benzothiazol-2-yl)-isonicotinamide or 2-[(2-dimethylamino-ethyl)-methyl-amino]-N-(4-methoxy-7-morpholin-4-yl-benzothiazol-2-yl)-isonicotinamide.

Further preferred are compounds of formula IA, wherein $R^1$ is morpholinyl, A is —CH$_2$— and R is —N(R")—(CH$_2$)$_m$—O-lower alkyl, S-lower alkyl, —N(R")$_2$, —N(R")—(CH$_2$)$_m$n-cycloalkyl or —N(R")—(CH$_2$)$_m$—C(O)O-lower alkyl, for example the following compounds:

2-[(2-methoxy-ethylamino)-methyl]-N-(4-methoxy-7-morpholin-4-yl-benzothiazol-2-yl)-isonicotinamide, 2-[(2-ethoxy-ethylamino)-methyl]-N-(4-methoxy-7-morpholin-4-yl-benzothiazol-2-yl)-isonicotinamide, 2-[(butyl-methyl-amino)-methyl]-N-(4-methoxy-7-morpholin-4-yl-benzothiazol-2-yl)-isonicotinamide, 2-butylaminomethyl-N-(4-methoxy-7-morpholin-4-yl-benzothiazol-2-yl)-isonicotinamide, 2-diethylaminomethyl-N-(4-methoxy-7-morpholin-4-yl-benzothiazol-2-yl)-isonicotinamide, N-(4-methoxy-7-morpholin-4-yl-benzothiazol-2-yl)-2-methylaminomethyl-isonicotinamide, 2-ethylaminomethyl-N-(4-methoxy-7-morpholin-4-yl-benzothiazol-2-yl)-isonicotinamide, 2-[(cyclopropylmethyl-amino)-methyl]-N-(4-methoxy-7-morpholin-4-yl-benzothiazol-2-yl)-isonicotinamide, 4-{[4-(4-methoxy-7-morpholin-4-yl-benzothiazol-2-yl-carbamoyl)-pyridin-2-yl-methyl]-amino}-butyric acid tert-butyl ester,

[4-(4-methoxy-7-morpholin-4-yl-benzothiazol-2-yl-carbamoyl)-pyridin-2-ylmethyl]-methyl-carbamic acid methyl ester, 2-ethylsulfanylmethyl-N-(4-methoxy-7-morpholin-4-yl-benzothiazol-2-yl)-isonicotinamide, 2-{[(2-ethoxy-ethyl)-methyl-amino]-methyl}-N-(4-methoxy-7-morpholin-4-yl-benzothiazol-2-yl)-isonicotinamide, 2-Ethylsulfanylmethyl-N-(4-methoxy-7-morpholin-4-yl-benzothiazol-2-yl)-isonicotinamide, 2-{[(2-Ethoxy-ethyl)-methyl-amino]-methyl}-N-(4-methoxy-7-morpholin-4-yl-benzothiazol-2-yl)-isonicotinamide Preferred are further compounds of formula IA, wherein $R^1$ is morpholinyl, A is —$CH_2$— and R is pyrrolidinyl, -2-oxo-pyrrolidinyl, piperidinyl, which is optionally substituted by lower alkoxy or hydroxy, or is morpholinyl or alkoxy, for example the following compounds:

N-(4-methoxy-7-morpholin-4-yl-benzothiazol-2-yl)-2-pyrrolidin-1-ylmethyl-isonicotinamide, N-(4-methoxy-7-morpholin-4-yl-benzothiazol-2-yl)-2-(2-oxo-pyrrolidin-1-yl-methyl)-isonicotinamide, N-(4-methoxy-7-morpholin-4-yl-benzothiazol-2-yl)-2-(4-methoxy-piperidin-1-ylmethyl)-isonicotinamide, N-(4-methoxy-7-morpholin-4-yl-benzothiazol-2-yl)-2-piperidin-1-ylmethyl-isonicotinamide, 2-(4-hydroxy-piperidin-1-ylmethyl)-N-(4-methoxy-7-morpholin-4-yl-benzothiazol-2-yl)-isonicotinamide, N-(4-methoxy-7-morpholin-4-yl-benzothiazol-2-yl)-2-morpholin-4-ylmethyl-isonicotinamide, 2-methoxymethyl-N-(4-methoxy-7-morpholin-4-yl-benzothiazol-2-yl)-isonicotinamide or 2-(4-hydroxy-piperidin-1-yl-methyl)-N-(4-methoxy-7-morpholin-4-yl-benzothiazol-2-yl)-isonicotinamide Preferred compound of the present application are compounds of formula IA, wherein $R^1$ is morpholinyl and A is —S—, for example the following compounds:

N-(4-methoxy-7-morpholin-4-yl-benzothiazol-2-yl)-2-methylsulfanyl-isonicotinamide or 2-ethylsulfanyl-N-(4-methoxy-7-morpholin-4-yl-benzothiazol-2-yl)-isonicotinamide.

Preferred compound of the present application are compounds of formula IA, wherein $R^1$ is morpholinyl and A—R are together -piperazinyl, substituted by lower alkyl, —C(O)-lower alkyl or an oxo group, or is piperidinyl, substituted by lower alkoxy or hydroxy, or is morpholinyl, substituted by lower alkyl, or is -cyclohexyl, -azetidin-1-yl, which is optionally substituted by hydroxy or lower alkoxy, or is -tetrahydopyran, or is 1,1-dioxo-thiomorpholinyl or 2-oxa-5-aza-bicyclo[2.2.1]hept-5-yl, for example the following compounds:

N-(4-methoxy-7-morpholin-4-yl-benzothiazol-2-yl)-2-(4-methyl-piperazin-1-yl)-isonicotinamide, 2-(4-acetyl-piperazin-1-yl)-N-(4-methoxy-7-morpholin-4-yl-benzothiazol-2-yl)-isonicotinamide, N-(4-methoxy-7-morpholin-4-yl-benzothiazol-2-yl)-2-(4-methyl-3-oxo-piperazin-1-yl)-isonicotinamide, 2-(4-ethyl-3-oxo-piperazin-1-yl)-N-(4-methoxy-7-morpholin-4-yl-benzothiazol-2-yl)-isonicotinamide, 2-[(2R,6S)-2,6-dimethyl-morpholin-4-yl]-N-(4-methoxy-7-morpholin-4-yl-benzothiazol-2-yl)-isonicotinamide, 2-cyclohexyl-N-(4-methoxy-7-morpholin-4-yl-benzothiazol-2-yl)-isonicotinamide, 2-azetidin-1-yl-N-(4-methoxy-7-morpholin-4-yl-benzothiazol-2-yl)-isonicotinamide, N-(4-methoxy-7-morpholin-4-yl-benzothiazol-2-yl)-2-(4-methoxy-piperidin-1-yl)-isonicotinamide, N-(4-methoxy-7-morpholin-4-yl-benzothiazol-2-yl)-2-(3-methoxy-piperidin-1-yl)-isonicotinamide, 2-(3-hydroxy-piperidin-1-yl)-N-(4-Methoxy-7-morpholin-4-yl-benzothiazol-2-yl)-isonicotinamide, N-(4-methoxy-7-morpholin-4-yl-benzothiazol-2-yl)-2-(tetrahydro-pyran-4-yl)-isonicotinamide, N-(4-methoxy-7-morpholin-4-yl-benzothiazol-2-yl)-2-{(1S,4S)-2-oxa-5-aza-bicyclo[2.2.1]hept-5-yl}-isonicotinamide, 2-(1,1-dioxo-1l6-thiomorpholin-4-yl)-N-(4-methoxy-7-morpholin-4-yl-benzothiazol-2-yl)-isonicotinamide, 2-(3-hydroxy-azetidin-1-yl)-N-(4-methoxy-7-morpholin-4-yl-benzothiazol-2-yl)-isonicotinamide, 2-(3-methoxy-azetidin-1-yl)-N-(4-methoxy-7-morpholin-4-yl-benzothiazol-2-yl)-isonicotinamide or 2-(3-ethoxy-azetidin-1-yl)-N-(4-methoxy-7-morpholin-4-yl-benzothiazol-2-yl)-isonicotinamide.

Preferred compound of the present application are compounds of formula IA, wherein $R^1$ is piperidinyl and A—R are together piperazinyl, substituted by lower alkyl, for example the following compound N-(4-methoxy-7-piperidin-1-yl-benzothiazol-2-yl)-2-(4-methyl-piperazin-1-yl)-isonicotinamide.

Preferred compound of the present application are compounds of formula IA, wherein $R^1$ is phenyl, A is —O— and R is lower alkyl, for example the following compound 2-methoxy-N-(4-methoxy-7-phenyl-benzothiazol-2-yl)-isonicotinamide.

Preferred are further compounds of formula IA, wherein $R^1$ is piperidinyl. Especially preferred are those compounds, wherein A is —$CH_2$— and R is pyrrolidinyl or morpholidinyl, for example the following compounds:

N-(4-methoxy-7-piperidin-1-yl-benzothiazol-2-yl)-2-pyrrolidin-1-yl-methyl-isonicotinamide or N-(4-methoxy-7-piperidin-1-yl-benzothiazol-2-yl)-2-morpholin-4-yl-methyl-isonicotinamide.

Compounds of formula IB are also preferred, for example those, wherein $R^1$ is morpholinyl, A is —O— and R is lower alkyl, —$(CH_2)_2$—O-lower alkyl or cycloalkyl, for example 6-methoxy-N-(4-methoxy-7-morpholin-4-yl-benzothiazol-2-yl)-nicotinamide, 6-isopropoxy-N-(4-methoxy-7-morpholin-4-yl-benzothiazol-2-yl)-nicotinamide, 6-(2-methoxy-ethoxy)-N-(4-methoxy-7-morpholin-4-yl-benzothiazol-2-yl)-nicotinamide or 6-cyclohexyloxy-N-(4-methoxy-7-morpholin-4-yl-benzothiazol-2-yl)-nicotinamide.

The present compounds of formulas IA and I-B and their pharmaceutically acceptable salts can be prepared by methods known in the art, for example, by processes described below, which processes comprise a) reacting a compound of formula

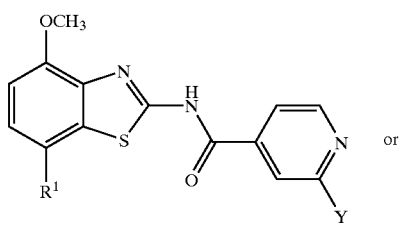
(4A)

or

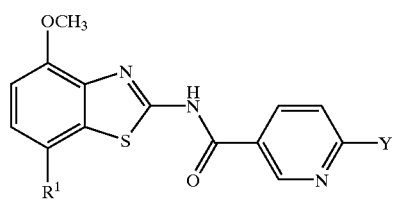
(4B)

with a compound of formula

H—A—R  (5)

in the presence of a base
to a compound of formula

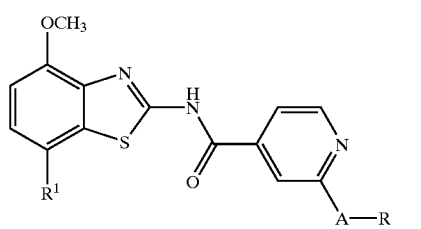
IA1 or

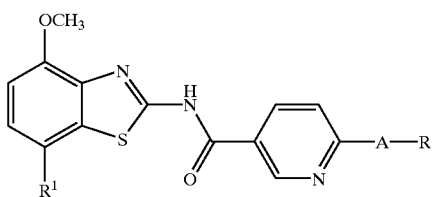
IB1 wherein R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl, —(CH$_2$)$_n$—N(R")$_2$, —(CH$_2$)$_n$-pyridinyl, —(CH$_2$)$_n$—CF$_3$, —(CH$_2$)$_n$-2-oxo-pyrrolidinyl or C$_{4-6}$-cycloalkyl, Y is chloro or bromo, A is O or S, and n is 1 or 2;

b) reacting a compound of formula

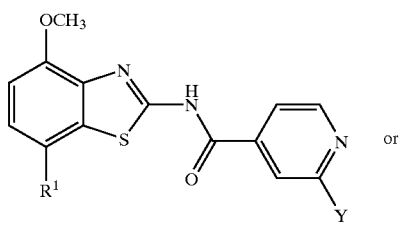
(4A)

or

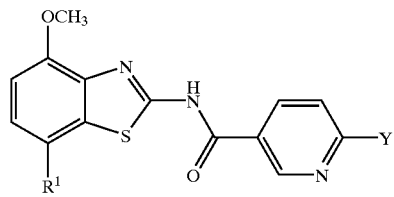
(4B)

with a compound of formula

HNRR'  (6)

to a compound of formula

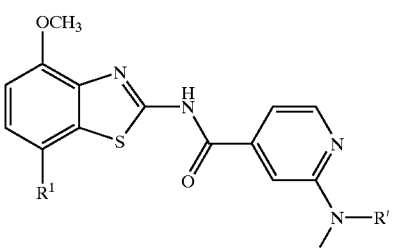
IA2 or

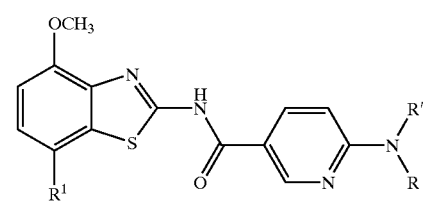
IB2 wherein R is lower alkyl, C$_{4-6}$-cycloalkyl, —(CH$_2$)$_n$—O-lower alkyl)-(CH$_2$)$_n$-pyridinyl, —(CH$_2$)$_n$-piperidinyl, (CH$_2$)$_n$-phenyl, —(CH$_2$)$_n$—N(R")—C(O)-lower alkyl, —(CH$_2$)$_n$-morpholinyl or —(CH$_2$)$_n$—N(R")$_2$ or R and R' form together with the N atom the following groups: piperazinyl, optionally substituted by lower alkyl, C(O)-lower alkyl or an oxo group, piperidinyl, optionally substituted by lower alkoxy or hydroxy, morpholinyl, optionally substituted by lower alkyl, azetidin-1-yl, optionally substituted by hydroxy or lower alkoxy, or thiomorpholine-1,1-dioxo or 2-oxa-bicyclo[2.21]hept-5-yl, R' and R" are independently from each other hydrogen or lower alkyl, Y is chloro or bromo and n is 1 or 2; or c) reacting a compound of formula

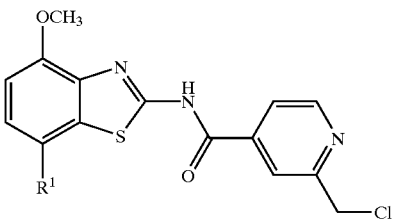
4A1 or

-continued

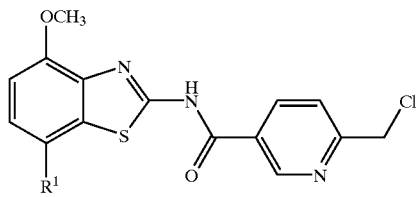
4B1 with a compound of formula

H—R    (9)

to a compound of formula

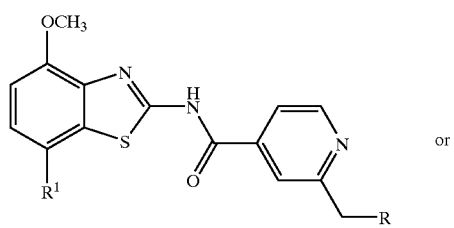
IA3-1 or

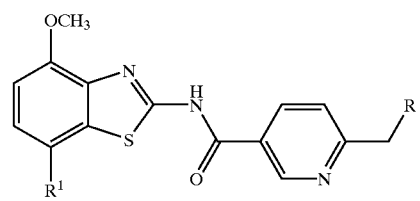
IB3-1 wherein R is —N(R")—(CH$_2$)$_m$—O-lower alkyl, —N(R")$_2$, —S-lower alkyl or is acetidinyl, pyrrolidinyl or piperidinyl, which are optionally substituted by hydroxy or lower alkoxy or is morpholinyl, —N(R")—(CH$_2$)$_m$—C$_{4-6}$-cycloalkyl, —N(R")—(CH$_2$)$_m$—C(O)O-lower alkyl, —N(R")—(CH$_2$)$_m$—C(O)OH, -2-oxo-pyrrolidinyl, —N(R")—C(O)O-lower alkyl, —O(CH$_2$)$_m$—O-lower alkyl or alkoxy, R" is independently from each other hydrogen or lower alkyl and m is 1, 2 or 3, or d) reacting a compound of formula

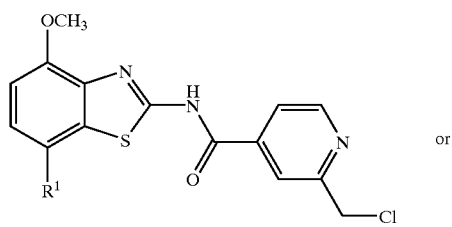
4A1 or

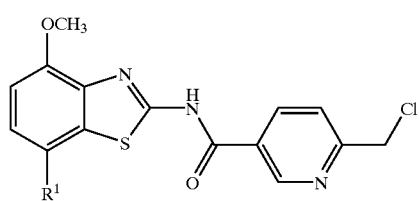
4B1 with a compound of formula

H—O—R    (5)

to give a compound of formula

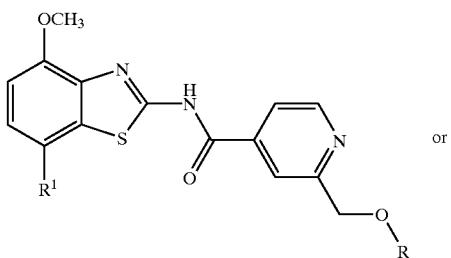
IA3-2 or

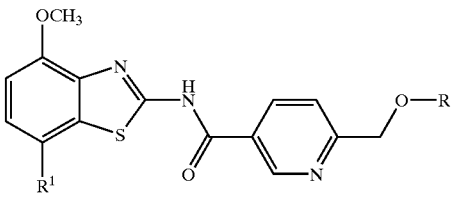
IB3-2 wherein R is —(CH$_2$)$_m$—O-lower alkyl or is lower alkyl and m is 1, 2 or 3, or e) reacting a compound of formula

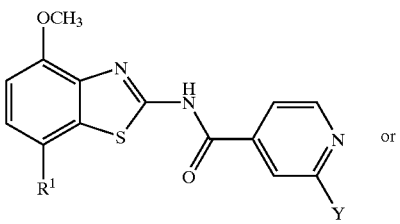
(4A)

or

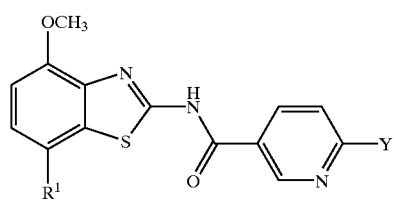
(4B)

with a compound of formula

Bu$_3$Sn—A'—R/cat or with B(OH)$_2$—A'—R/cat to a compound of formula

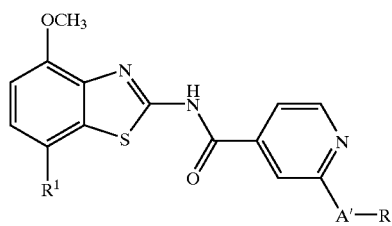
IA4 or

-continued

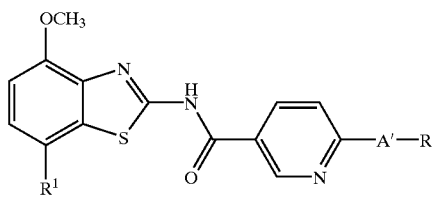

IB4 wherein A'—R are together $C_{4-6}$-cycloalkenyl or dihydopyran and Y is bromo, and then reacting a compound of formula IA4 or IB4 with hydrogen and a catalyst to give a compound of formula

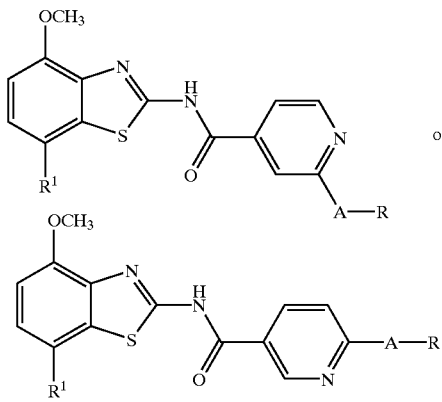

IA5 or

IB5 wherein A—R are together $C_{4-6}$-cycloalkyl or tetrahydropyran, and
if desired, converting the compounds obtained into pharmaceutically acceptable acid addition salts.

The compounds of formulae IA and IB may be prepared in accordance with process variants a) to e) and with the following schemes 1 to 10.

Preparation of Compounds of Formula IA or IB, Wherein A is —O— or —S— and R is —(CH$_2$)$_n$—N(R")—C(O)-Lower Alkyl, —(CH$_2$)$_n$—O-Lower Alkyl, —(CH$_2$)$_n$—O—(CH$_2$)$_n$—O-Lower Alkyl, Lower Alkyl, —(CH$_2$)$_n$-Morpholinyl, —(CH$_2$)-Phenyl, —(CH)$_n$—N(R")$_2$, —(CH$_2$)$_n$-Pyridinyl, —(CH$_2$)$_n$—CF$_3$, —(CH$_2$)$_n$-2-oxo-Pyrrolidinyl or $C_{4-6}$-Cycloalkyl and n is 1 or 2

One method of preparation of compounds of formula IA1 or IB1, wherein A is oxygen or sulfur, is from 2-chloro- or 2-bromo-isonicotinamide intermediates of formula (4A) or from 2-chloro- or 2-bromo-nicotinamide intermediates of formula (4B), the preparation of which is shown in reaction schemes 1 and 2 below.

Scheme 1

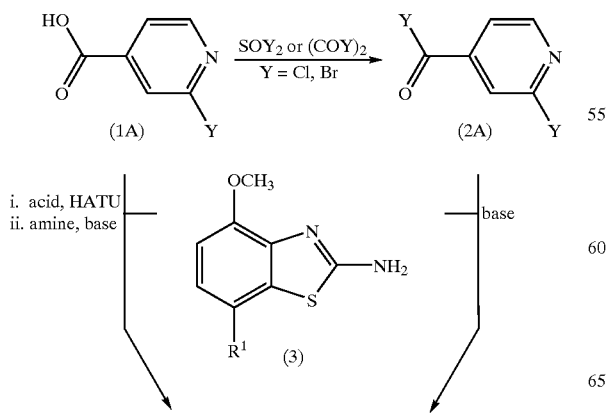

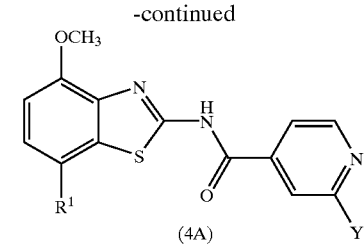

(4A)

Y = Cl, Br

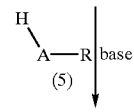

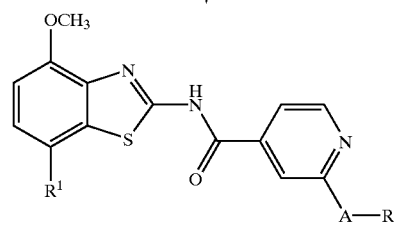

IA1 wherein R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl, —(CH$_2$)$_n$—N(R")$_2$, —(CH$_2$)$_n$-pyridinyl, —(CH$_2$)$_n$—CF$_3$, —(CH$_2$)$_n$-2-oxo-pyrrolidinyl or $C_{4-6}$-cycloalkyl, A is O or S, and n is 1 or 2.

HATU is O-(7-azabenzotriazol-1-yl)-N,N,N',N'-tetramethyluronium hexafluorophosphate.

Scheme 2

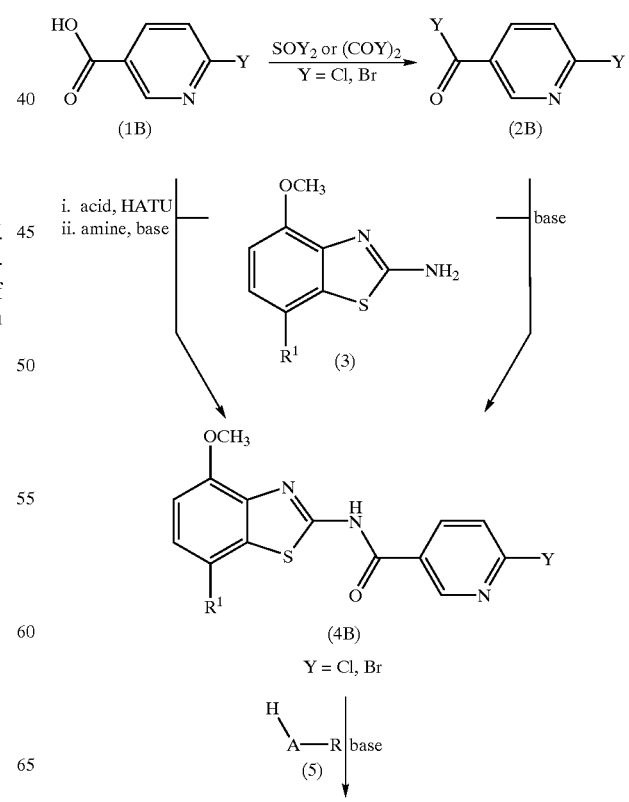

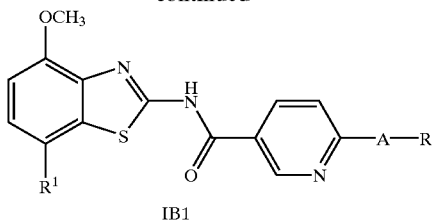

IB1 wherein R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl) —(CH$_2$)$_n$—N(R")$_n$, —(CH$_2$)$_n$-pyridinyl, —(CH$_2$)$_n$—CF$_3$, —(CH$_2$)$_n$-2-oxo-pyrrolidinyl or C$_{4-6}$-cycloalkyl, A is O or S, and n is 1 or 2.

HATU is O-(7-azabenzotriazol-1-yl)-N,N,N',N'-tetramethyluronium hexafluorophosphate.

Preparation of Compounds of Formula (2A) or (2B)

The starting 2-chloroisonicotinic acid or 2-bromoisonicotinic acid of formula (1A) or 2-chloronicotinic acid or 2-bromonicotinic acid of formula (IB) may be obtained commercially, for example from Maybridge Chemicals, or may be prepared according to methods well known in the art.

The 2-haloisonicotinic acid of formula (1A) or 2-halonicotinic acid of formula (IB) may be converted to the corresponding acyl halide derivative of formula (2A) or (2B) by reacting a compound of formula (1A) or (1B) with an excess of a halogenating agent, such as oxalyl chloride or oxalyl bromide, or thionyl chloride or thionyl bromide, using a catalyst such as N,N-dimethylformamide or pyridine, in an organic solvent, prefereably dichloromethane or dichloroethane, at room temperature for about 2–16 hours, preferably 16 hours. The product of formula (2) is isolated by conventional means, and preferably reacted in the next step without further purification.

Preparation of Compounds of Formula (4A) or (4B)

The starting 2-amino-benzothiazole compounds of formula (3) may be prepared according to methods disclosed in EP 00113219.0.

The compounds of formula (4A) or (4B) are prepared by treating the 2-amino-benzothiazole compounds of formula (3) with a slight excess of the acyl halide compounds of formula (2A) or (2B) in a non-protic organic solvent, preferably a mixture of dichloromethane and tetrahydrofuran, containing a base, preferably N-ethyldiisopropylamine or triethylamine, at room temperature for 2–24 hours, preferably 24 hours. The product of formula (4A) or (4B) is isolated by conventional means, and preferably purified by means of chromatography or recrystallisation.

Alternative Preparation of Compounds of Formula (4A) or (4B)

The compounds of formula (4A) or (4B) may also be prepared directly from compounds of formula (2A) or (2B).

In this method, the compound of formula (2A) or 2(B) is treated with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-ethyldiisopropylamine, at room temperature for 30–90 minutes. This mixture is then treated with a 2-amino-benzothiazole compound of formula (3) in a solvent mixture, preferably a mixture of tetrahydrofuran, dioxane and N,N-dimethylformamide, at room temperature for 16–24 hours, preferably 24 hours. The product of formula (4) is isolated by conventional means, and preferably purified by means of chromatography or recrystallisation.

Preparation of Compounds of Formula IA1 or IB1 (A is Oxygen or Sulfur)

One method of preparation of compounds of formula IA1 or IB1, is by treatment of a compound of formula (4A) or (4B) with an excess of an appropriate alcohol or thiol of formula (5), which may be commercially available or may be prepared by methods well known in the art, and which may be chosen from: a primary or secondary aliphatic alcohol or thiol, or an aromatic alcohol or thiol, in each case used together with a metal-hydride base, preferably sodium hydride or potassium hydride. These reactions may be carried out in an ethereal solvent such as such as dioxane, tetrahydrofuran or 1,2-dimethoxyethane, preferably dioxane, optionally containing a co-solvent such as N,N-dimethylformamide, at a temperature between room temperature and the reflux temperature of the solvent, preferably about 100° C., for 2–72 hours, preferably 16 hours. The product of Formula I, where A is oxygen or sulfur, is isolated by conventional means, and preferably purified by means of chromatography or recrystallisation.

Preparation of Compounds of Formula IA2 and IB2, Wherein A is —N(R')— and R is Lower Alkyl, C$_{4-6}$-Cycloalkyl, —(CH$_2$)$_n$—O-Lower Alkyl, —(CH$_2$)$_n$-Pyridinyl, —(CH$_2$)$_n$-Piperidinyl, —(CH$_2$)$_n$-Phenyl, —(CH$_2$)$_n$—N(R")—C(O)-Lower Alkyl, —(CH$_2$)$_n$-Morpholinyl or —(CH$_2$)$_n$—N(R")$_2$ or R and R' Form Together with the N Atom the Following Groups: Piperazinyl, Optionally Substituted by Lower Alkyl, C(O)-Lower Alkyl or an Oxo Group, Piperidinyl, Optionally Substituted by Lower Alkoxy or Hydroxy, Morpholinyl, Optionally Substituted by Lower Alkyl, Azetidin-1-yl, Optionally Substituted by Hydroxy or Lower Alkoxy, or Thiomorpholine-1,1-dioxo or 2-oxa-Bicyclo[2.21]hept-5-yl, R' and R"0 are Independently From Each Other Hydrogen or Lower Alkyl, Y is Bromo and n is 1 or 2

One method of preparation of compounds of formula IA1 and IB1 is from 2-bromoisonicotinamide intermediates of formula (4A) or from 2-chloro- or 2-bromonicotinamide intermediates of formula (4B), as shown in reaction schemes 3 and 4 below.

Scheme 3

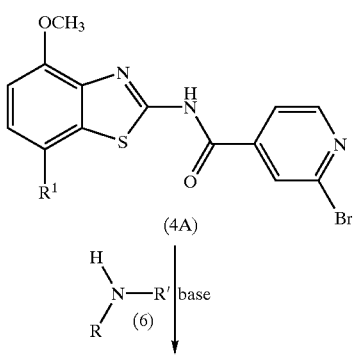

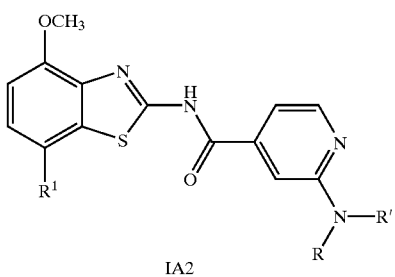

R is lower alkyl, $C_{4-6}$-cycloalkyl, —$(CH_2)_n$—O-lower alkyl, —$(CH_2)_n$-pyridinyl, —$(CH_2)_n$-piperidinyl, —$(CH_2)_n$-phenyl, —$(CH_2)_n$—N(R")—C(O)-lower alkyl, —$(CH_2)_n$-morpholinyl or —$(CH_2)_n$—N(R")$_2$ or R and R' form together with the N atom the following groups: piperazinyl, optionally substituted by lower alkyl, C(O)-lower alkyl or an oxo group, piperidinyl, optionally substituted by lower alkoxy or hydroxy, morpholinyl, optionally substituted by lower alkyl, azetidin-1-yl, optionally substituted by hydroxy or lower alkoxy, or thiomorpholine-1,1-dioxo or 2-oxa-bicyclo[2.21]hept-5-yl. R' and R" are independently from each other hydrogen or lower alkyl, Y is bromo, R' and R" are independently from each other hydrogen or lower alkyl and n is 1 or 2.

Scheme 4

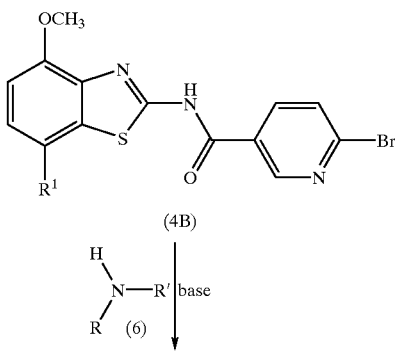

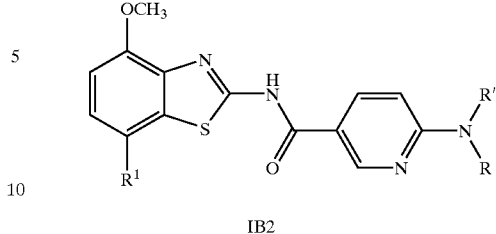

R is lower alkyl, $C_{4-6}$-cycloalkyl, —$(CH_2)_n$-lower alkyl, —$(CH)_n$-pyridinyl, —$(CH_2)_n$-piperidinyl, —$(CH_2)_n$-phenyl, —$(CH_2)_n$—N(R")—C(O)-lower alkyl, —$(CH_2)_n$-morpholinyl or —$(CH_2)_n$—N(R")$_2$ or R and R' form together with the N atom the following groups: piperazinyl, optionally substituted by lower alkyl, C(O)-lower alkyl or an oxo group, piperidinyl, optionally substituted by lower alkoxy or hydroxy, morpholinyl, optionally substituted by lower alkyl, azetidin-1-yl, optionally substituted by hydroxy or lower alkoxy, or thiomorpholine-1,1-dioxo or 2-oxa-bicyclo[2.2 1]hept-5-yl, R' and R" are independently from each other hydrogen or lower alkyl, Y is chloro or bromo, R' and R" are independently from each other hydrogen or lower alkyl and n is 1 or 2.

To prepare the compounds of formula IA2 or IB2, the 2-bromo-isonicotinamide intermediate of formula (4A) or the 2-chloro- or 2-bromo-nicotinamide intermediate of formula (4B) is treated with a large excess of an appropriate amine of formula (6), which may be commercially available or may be prepared by methods well known in the art, and which may be chosen from: a primary or secondary aliphatic amine or an aromatic amine, in each case used together with a metal carbonate base, preferably cesium carbonate. These reactions may be carried out in the absence of added solvent, or optionally in the presence of a solvent such as N,N-dimethylformamide or N-methylpyrrolidone, at an elevated temperature, preferably about 140° C., for 2–48 hours, preferably 24 hours. The product of formula IA2 or IB2, where A is nitrogen, is isolated by conventional means, and preferably purified by means of chromatography or recrystallisation.

Preparation of Compounds of Formula IA or IB, Wherein A is —$CH_2$— and R is —N(R")—$(CH_2)_m$—O-Lower Alkyl, —N(R")$_2$, —S-Lower Alkyl or is Acetidinyl, Pyrrolidinyl or Piperidinyl, Which are Optionally Substituted by Hydroxy or Lower Alkoxy or is Morpholinyl, —N(R")—$(CH_2)_m$—$C_{4-6}$-Cycloalkyl, —N(R")—$(CH_2)_m$—C(O)O-Lower Alkyl, —N(R")—$(CH_2)_m$—C(O)OH, -2-oxo-Pyrrolidinyl, —N(R")—C(O)O-Lower Alkyl, —O$(CH_2)_m$—O-Lower Alkyl or Alkoxy, R" is Independently From Each Other Hydrogen or Lower Alkyl and m is 1, 2 or 3

One method of preparation of compounds of formula IA or IB, wherein A is $CH_2$, is from 2-chloromethyl-isonicotinamide intermediates of formula (4A1) or from 2-chloromethyl-nicotinamide intermediates of formula (4B1), as shown in reaction scheme 5 an 6 below.

Scheme 5

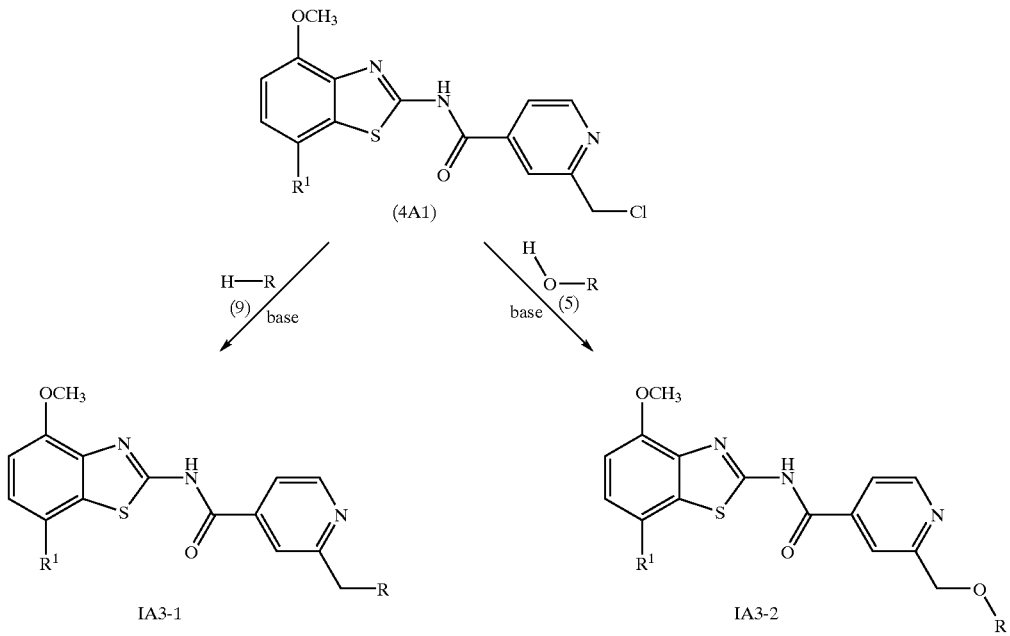

wherein R in this scheme for compounds of formula IA3-1 is —N(R")—(CH$_2$)$_m$—O-lower alkyl, —N(R")$_2$, —S-lower alkyl or is acetidinyl, pyrrolidinyl or piperidinyl, which are optionally substituted by hydroxy or lower alkoxy, or is morpholinyl, —N(R")—(CH$_2$)$_m$—C$_{4-6}$-cycloalkyl, N(R")—(CH$_2$)$_m$—C(O)O-lower alkyl, —N(R")—(CH$_2$)$_m$—C(O)OH, -2-oxo-pyrrolidinyl or —N(R")—C(O)O-lower alkyl, R" is independently from each other hydrogen or lower alkyl and m is 1, 2 or 3, and R in this scheme for compounds of formula IA3-2 is —(CH$_2$)$_m$—O-lower alkyl or alkyl;

wherein R in this scheme for compounds of formula IB3-1 is —N(R")—(CH$_2$)$_m$—O-lower alkyl, —N(R")$_2$, —S-lower alkyl or is acetidinyl, pyrrolidinyl or piperidinyl, which are optionally substituted by hydroxy or lower alkoxy, or is morpholinyl, —N(R")—(CH$_2$)$_m$—C$_{4-6}$-cycloalkyl, N(R")—(CH$_2$)$_m$—C(O)O-lower alkyl, —N(R")—(CH$_2$)$_m$—C(O)OH, -2-oxo-pyrrolidiinyl, —N(R")—C(O)O-lower alkyl, R" is independently from each other hydrogen or lower alkyl and m is 1, 2 or 3, and R in this scheme for compounds of formula IB3-2 is —(CH$_2$)$_m$—O-lower alkyl or alkyl, R" is hydrogen or lower alkyl, and m is 1, 2 or 3.

Scheme 6

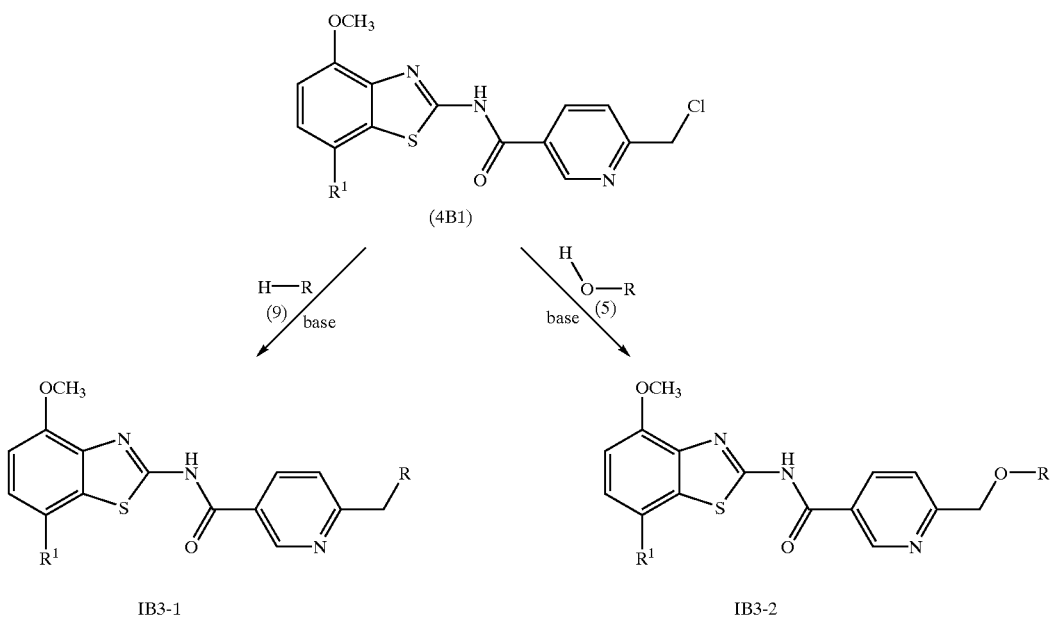

One method of preparation of compounds of formulae IA3-1 or IA3-2 and IB3-1 or IB3-2 is from the appropriately substituted benzothiazol-2-yl-amine (3) and 2-chloromethyl-isonicotinoyl chloride (4A1) or 2-chloromethyl-nicotinoyl chloride (4B1) as shown in reaction schemes 7 and 8 below.

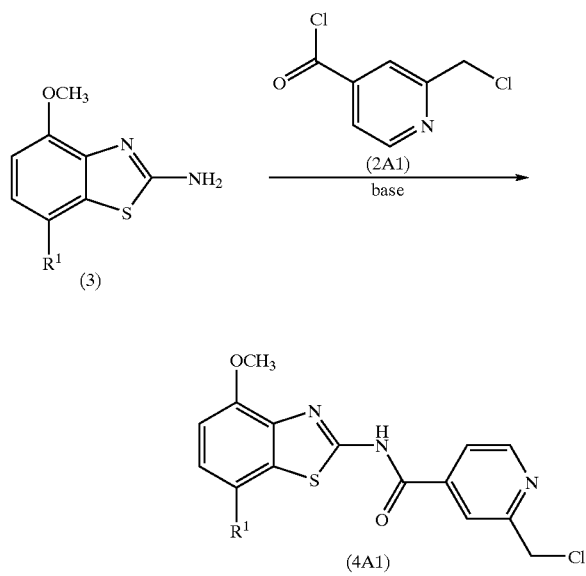

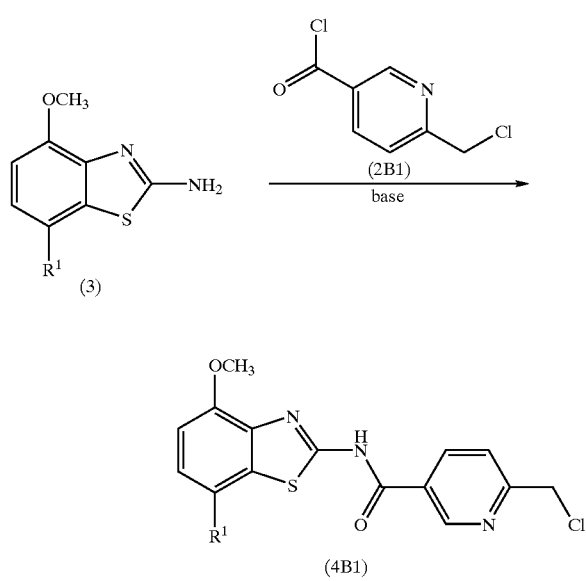

Preparation of Compounds of Formula IA or IB, Wherein A is —CH$_2$— and R is —O(CH$_2$)$_m$—O-Lower Alkyl or Alkoxy One method of preparation of compounds of formula IA3-1, IA3-2, IB3-1 or IB3-2 is by treatment of a compound of formula (4A1) or (4B1) with an excess of an appropriate alcohol of formula (5), which may be commercially available or maybe prepared by methods well known in the art, and which may be chosen from: a primary or secondary aliphatic alcohol or an aromatic alcohol, in each case used together with a metal-hydride base, preferably sodium hydride or potassium hydride. These reactions may be carried out in an ethereal solvent such as dioxane, tetrahydrofuran or 1,2-dimethoxyethane, preferably dioxane, optionally containing a co-solvent such as N,N-dimethylformamide, or in the respective alcohol as solvent, at a temperature between room temperature and the reflux temperature of the solvent, preferably about 100° C., for 2–72 hours, preferably 16 hours. The product of Formula I, where A is CH$_2$O, is isolated by conventional means, and preferably purified by means of chromatography or recrystallisation.

Preparation of Compounds of Formula IA or IB, Wherein A is —CH$_2$— and R is —N(R")—(CH$_2$)$_m$—O-Lower Alkyl, —N(R")$_2$, or is Acetidinyl, Pyrrolidinyl or Piperidinyl, Which are Optionally Substituted by Hydroxy or Lower Alkoxy or is Morpholinyl, —N(R")—(CH$_2$)$_m$—C$_{4-6}$-Cycloalkyl, —N(R")—(CH$_2$)$_m$—C(O)O-Lower Alkyl, —N(R")—(CH$_2$)$_m$—C(O)OH, -2-oxo-Pyrrolidinyl, —N(R")—C(O)O-Lower Alkyl, R" is Independently From Each Other Hydrogen or Lower Alkyl and m is 1, 2 or 3

To prepare the compounds of formula IA or IB, wherein A is —CH$_2$—, the 2-chloro-isonicotinamide intermediate of formula (4A1) or (4B1) is treated with a large excess of an appropriate amine of formula (9), which may be commercially available or may be prepared by methods well known in the art, and which may be chosen from: a primary or secondary aliphatic amine or an aromatic amine. These reactions may be carried out in the absence of added solvent, or optionally in the presence of a solvent such as N,N-dimethylformamide or N-methylpyrrolidone, at an elevated temperature, preferably about 60° C., for 2–48 hours, preferably 4 hours. The product of formula I, where A is CH$_2$, is isolated by conventional means, and preferably purified by means of chromatography or recrystallisation.

Preparation of Compounds of Formula I, Wherein A—R are Together C$_{4-6}$-Cycloalkyl or Tetrahydropyran One method of preparation of compounds of formula IA4 or IB4 and IA5 or IB5 is shown in reaction schemes 9 and 10 below.

Scheme 9

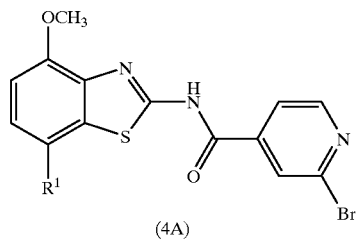

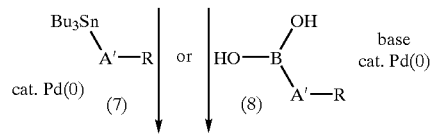

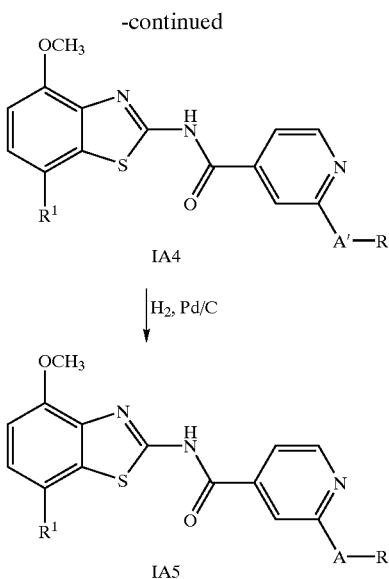

IA4

↓ H₂, Pd/C

IA5 wherein A'—R are together C₄₋₆-cycloalkenyl or dihydropyran and A—R are together C₄₋₆-cycloalkyl or tetrahydropyran.

Scheme 10

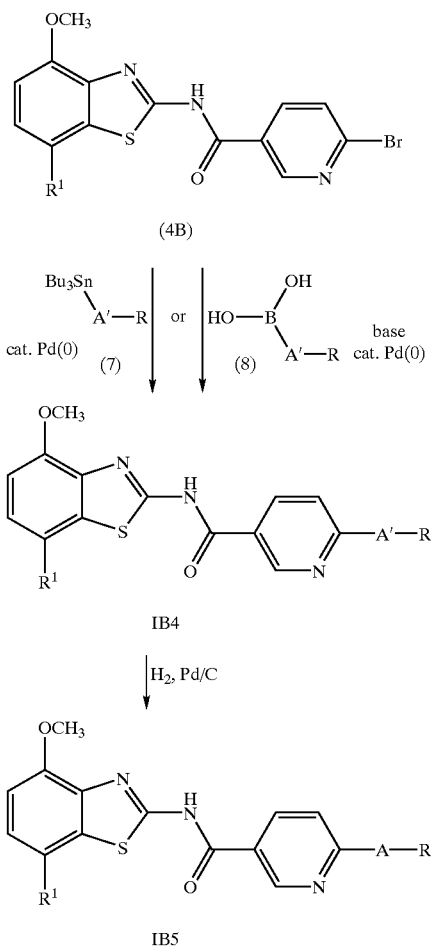

wherein A'—R are together C₄₋₆-cycloalkenyl or dihydropyran and A—R are together C₄₋₆-cycloalkyl or tetrahydropyran.

Preparation of Compounds of Formula IA4 and IB4

The starting tributylstannane compounds of formula (7) may be obtained commercially, for example from Fluka, or may be prepared according to methods well known in the art.

The compounds of formula IA4 or IB4 are prepared by treating 2-bromo-isonicotinamide intermediates of formula (4A) or 2-bromo-nicotinamide intermediates of formula (4B) with an excess of a tributylstannane compound of formula (7) in an organic solvent, preferably N,N-dimethylformamide, containing a palladium catalyst, preferably bis(triphenylphosphine)palladium(II) chloride, and in the presence of other additives such as triphenylphosphine, lithium chloride and 2,6-di-tert-butyl-4-methylphenol. The reaction is carried out at elevated temperature, preferably about 100° C., for about 16–96 hours, preferably about 72 hours. The product of formula IA4 or IB4 is isolated by conventional means, and preferably purified by means of chromatography or recrystallisation.

Alternative Preparation of Compounds of Formula IA4 or IB4

The starting boronic acid compounds of formula (8) may be obtained commercially, for example from Fluka, or may be prepared according to methods well known in the art.

The compounds of formula IA4 or IB4 may alternatively be prepared by treating 2-bromo-isonicotinamide intermediates of formula (4A) or 2-bromo-nicotinamide intermediates of formula (4B) with an excess of a boronic acid compound of formula (8). The reaction is carried out in an aqueous solvent, preferably a mixture of water and dioxane, containing a palladium catalyst, preferably bis(triphenylphosphine)palladium(II) chloride, and an inorganic base, preferably sodium carbonate. The reaction is preferably carried out in the presence of other additives such as triphenylphosphine, lithium chloride and 2,6-di-tert-butyl-4-methylphenol. The reaction is preferably carried out at the reflux temperature of the solvent, preferably about 100° C., for about 16–96 hours, preferably about 48 hours. The product of formula IA4 or IB4 is isolated by conventional means, and preferably purified by means of chromatography or recrystallisation.

Preparation of Compounds of Formula IA5 and IB5

One method of preparation of compounds of formula IA5 or IB5 is by hydrogenation of a compound of formula IA4 or IB4 in the presence of a hydrogenation catalyst, preferably 10% palladium on charcoal. These reactions may be carried out in a mixture of organic solvents, preferably a mixture of methanol and dichloromethane, at room temperature and at a pressure of one atmosphere or above, preferably at one atmosphere, for 2–48 hours, preferably about 16 hours. The product of formula IA5 or IB5, where A is carbon, is isolated by conventional means, and preferably purified by means of chromatography or recrystallisation.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula IA and IB

The compounds of Formula IA or IB may be basic, for example in cases where the residue A—R contains a basic group such as an aliphatic or aromatic amine moiety. In such cases the compounds of Formula IA or IB may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of Formula IA and IB may be converted to the corresponding free bases by treatment with at least a stoichiometric equivalent of a suitable base such as sodium or potassium hydroxide, potassium carbonate, sodium bicarbonate, ammonia, and the like.

The compounds of formulas IA and IB and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-583261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminiase in a final volume of 200 µl of buffer A. Non-specific binding was defined using xainthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The preferred compounds show a pKi>8.5. In the list below are described some affinity data to the $hA_2$-receptor:

| Example No. | $hA_2$ (pKi) | Example No. | $hA_2$ (pKi) |
| --- | --- | --- | --- |
| 1 | 8.50 | 73 | 8.74 |
| 3 | 8.51 | 74 | 8.87 |
| 4 | 8.58 | 75 | 8.72 |
| 5 | 8.58 | 76 | 8.76 |
| 6 | 8.94 | 77 | 8.54 |
| 8 | 8.75 | 80 | 8.68 |
| 10 | 9.14 | 81 | 8.62 |
| 13 | 8.81 | 83 | 8.76 |
| 15 | 8.72 | 85 | 8.53 |
| 17 | 8.63 | 86 | 9.30 |
| 18 | 9.21 | 87 | 9.07 |
| 24 | 8.65 | 88 | 9.34 |
| 26 | 9.02 | 89 | 8.83 |
| 31 | 9.00 | 90 | 8.76 |
| 35 | 8.70 | 92 | 8.80 |
| 40 | 8.99 | 93 | 8.97 |
| 44 | 8.52 | 94 | 8.92 |
| 47 | 8.6 | 95 | 8.72 |
| 52 | 8.8 | 96 | 8.79 |
| 54 | 8.7 | 97 | 8.65 |
| 56 | 8.8 | 99 | 9.22 |
| 58 | 8.7 | 100 | 8.81 |
| 62 | 8.8 | 101 | 8.90 |
| 65 | 8.5 | 102 | 8.70 |
| 70 | 8.9 | 103 | 8.80 |
| 71 | 8.7 | 104 | 8.50 |

The compounds of formula IA and IB and the pharmaceutically acceptable salts of the compounds of formula IA and IB can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula IA and IB can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, maskin, agents or antioxidants. They can also contain still other therapeutically valuable substances.

Medicaments containing a compound of formula IA and IB or a pharmaceutically acceptable salt thereof and a therapeutically inert carrier are also an object of the present invention, as is a process for their production, which comprises bringing one or more compounds of formula IA and IB and/or pharmaceutically acceptable acid addition salts and, if desired, one or more other therapeutically valuable substances into a galenical administration form together with one or more therapeutically inert carriers.

In accordance with the invention compounds of formula IA and IB as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Lactose Anhydrous DTC | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

2-(2-Methoxy-ethoxy)-N-(4-methoxy-7-morpholin-4-yl-benzothiazol-2-yl)-isonicotinamide a) 2-Chloro-N-(4-methoxy-7-morpholin-4-yl-benzothiazol-2-yl)-isonicotinamide To a stirred solution of 10.8 g (40.8 mmol) 4-methoxy-7-morpholin-4-yl-benzothiazol-2-ylamine and 17.3 ml (102 mmol) N-ethyldiisopropylamine in 500 ml THF at 5° C. was added dropwise over 90 minutes a solution of 7.90 g (44.9 mmol) 2-chloro-isonicotinoyl chloride in 250 ml dichloromethane and stirring continued at room temperature for 16 h. The reaction mixture was then quenched by addition of 30 ml methanol and concentrated in vacuo. The residue was then resuspended in ethyl acetate and washed sequentially with saturated sodium bicarbonate solution, 0.5 M hydrochloric acid and saturated brine. The organic phase was then dried over sodium sulfate and concentrated in Vacuo to ca 100 ml. The resulting suspension was then left standing at room temperature for 72 h and then 100 ml ether was added and the suspension stirred for 1 hour at room temperature. The crystals were collected by filtration and dried in vacuo to afford 9.79 g (59%) 2-chloro-N-(4-methoxy-7-morpholin-4-yl-benzothiazol-2-yl)-isonicotinamide as a brown crystalline solid. ES-MS m/e (%): 429 (M$\{^{37}$Cl$\}$+Na$^+$, 11), 427 (M$\{^{35}$Cl$\}$+Na$^+$, 30). 407 (M$\{^{37}$Cl$\}$+H$^+$, 30), 405 (M$\{^{35}$Cl$\}$+H$^+$, 100).

b) 2-(2-Methoxy-ethoxy)-N-(4-methoxy-7-morpholin-4-yl-benzothiazol-2-yl-isonicotinamide To a stirred solution of 0.058 ml (0.74 mmol) 2-methoxyethanol in 2 ml dioxane at room temperature was added 49 mg (1.24 mmol) sodium hydride (60% dispersion in mineral oil) and stirring continued for 10 minutes. 200 mg (0.49 mmol) 2-chloro-N-(4-methoxy-7-morpholin-4-yl-benzothiazol-2-yl)-isonicotinamide was then added and the mixture heated at 115° C. for 16 h. The reaction mixture was then cooled to room temperature, diluted with ethyl acetate, and washed sequentially with 1 M hydrochloric acid and saturated brine. The organic phase was then dried over sodium sulfate and concentrated in vacuo. Flash chromatography (2/1 ethyl acetate/toluene) afforded 109 mg (50%) 2-(2-methoxy-ethoxy)-N-(4-methoxy-7-morpholin-4-yl-benzothiazol-2-yl)-isonicotinamide as a yellow crystalline solid. ES-MS m/e (%): 467 (M+Na$^+$, 16), 445 (M+H$^+$, 100).

In an analogous manner there was obtained:

EXAMPLE 2

2-[2-(2-Methoxy-ethoxy)-ethoxy]-N-(4-methoxy-7-morpholin-4-yl-benzothiazol-2-yl)-isonicotinamide From 2-chloro-N-(4-methoxy-7-morpholin-4-yl-benzothiazol-2-yl)-isonicotinamide with sodium hydride and diethylene glycol monomethyl ether in dioxane. ES-MS m/e (%): 511 (M+Na$^+$, 13), 489 (M+H$^+$, 100).

EXAMPLE 3

2-Ethoxy-N-(4-methoxy-7-morpholin-4-yl-benzothiazol-2-yl)-isonicotinamide a) 2-Bromo-isonicotinic Acid To a stirred solution of 29.0 g (169 mmol) 2-bromo-4-methylpyridine in 150 ml concentrated sulfuric acid was added portionwise 67.9 g (231 mmol) potassium dichromate and the reaction mixture was cooled with an ice bath so that the temperature stayed between 20–50° C. After the addition was complete, stirring was continued at room temperature for a further 2 h. The reaction mixture was then poured slowly onto 2 l ice-water and the mixture stirred for 1 hour at room temperature. The resulting crystals were collected by filtration, washed with water until the washings were colourless, and dried in vacuo to afford 30.0 g (88%)) 2-bromo-isonicotinic acid as a white crystalline solid. El-MS m/e (%)): 203 (M$\{^{81}$Br$\}^+$, 100), 201 (M$\{^{79}$Br$\}^+$, 93). 122 ([M-Br]$^+$, 98).

b) 2-Bromo-N-(4-methoxy-7-morpholin-4-yl-benzothiazol-2-yl)-isonicotinamide

To a stirred solution of 3.81 g (18.8 mmol) 2-bromo-isonicotinic acid in 50 ml THF were added 7.16 g (18.8 mmol) HATU and 3.21 ml (18.8 mmol) N-ethyldiisopropylamine and stirring continued at room temperature for 90 minutes. A solution of 5.00 g (18.8 mmol) 4-methoxy-7-morpholin-4-yl-elenzothiazol-2-ylamine in 50 ml dioxane and 10 ml DMF was then added and stirring continued at room temperature for 16 h. The reaction mixture was then poured into 300 ml 1 M hydrochloric acid and the mixture stirred for 20 min. The resulting crystals were collected by filtration, washed with water and then with ether, and dried in vacuo to afford 7.53 g (89%) 2-bromo-N-(4-methoxy-7-morpholin-4-yl-benzothiazol-2-yl)-isonicotinamide as a yellow crystalline solid. ES-MS m/e (%): 473 (M$\{^{81}$Br$\}$+Na$^+$, 30), 471 (M$\{^{79}$Br$\}$+Na$^+$, 34). 451 (M$\{^{81}$Br$\}$+H$^+$, 100), 449 (M$\{^{79}$Br$\}$+H$^+$, 80).

c) 2-Ethoxy-N-(4-methoxy-7-morpholin-4-yl-benzothiazol-2-yl)-isonicotinamide

To a stirred solution of 0.52 ml (8.90 mmol) ethanol in 30 ml dioxane at room temperature was added 486 mg (11.1 mmol) sodium hydride (55% dispersion in mineral oil) and the mixture heated at 50° C. for 30 minutes. 1.00 g (2.23 mmol) 2-bromo-N-(4-methoxy-7-morpholin-4-yl-benzothiazol-2-yl)-isonicotinamide was then added and the mixture heated at 115° C. for 72 h. The reaction mixture was then cooled to room temperature and concentrated in vacuo. The residue was resuspended in dichloromethane, and washed sequentially with water and saturated brine. The organic phase was then dried over sodium sulfate and concentrated in vacuo. The residue was resuspended in methanol and concentrated in vacuo to 2 ml, 20 ml ether added, and the resulting crystals were collected by filtration and dried in vacuo to afford 410 mg (44%) 2-ethoxy-N-(4-methoxy-7-morpholin-4-yl-benzothiazol-2-yl)-isonicotinamide as a light yellow crystalline solid.

ES-MS m/e (%): 437 (M+Na$^+$, 24), 414 (M+H$^+$, 100). Analogously to Example 1 there were obtained:

EXAMPLE 4

2-Benzyloxy-N-(4-methoxy-7-morpholin-4-yl-benzothiazol-2-yl)-isonicotinamide

From 2-chloro-N-(4-methoxy-7-morpholin-4-yl-benzothiazol-2-yl)-isonicotinamide with sodium hydride and benzyl alcohol in dioxane. ES-MS m/e (%): 499 (M+Na$^+$, 40), 477 (M+H$^+$, 100).

EXAMPLE 5

2-Methoxy-N-(4-methoxy-7-morpholin-4-yl-benzothiazol-2-yl)-isonicotinamide

From 2-chloro-N-(4-methoxy-7-morpholin-4-yl-benzothiazol-2-yl)-isonicotinamide with sodium hydride and methanol in dioxane and DMF. ES-MS m/e (%): 423 (M+Na$^+$, 31), 401 (M+H$^+$, 100).

EXAMPLE 6

N-(4-Methoxy-7-morpholin-4-yl-benzothiazol-2-yl)-2-(pyridin-2-ylmethoxy)-isonicotinamide From 2-chloro-N-(4-methoxy-7-morpholin-4-yl-benzothiazol-2-yl)-isonicotinamide with sodium hydride and 2-hydroxymethylpyridine in dioxane. ES-MS m/e (%): 500 (M+Na$^+$, 23), 478 (M+H$^+$, 100).

EXAMPLE 7

N-(4-Methoxy-7-morpholin-4-yl-benzothiazol-2-yl)-2-[methyl-(2-pyridin-2-yl-ethyl)-amino]-isonicotinamide A stirred suspension of 200 mg (0.45 mmol) 2-bromo-N-(4-methoxy-7-morpholin-4-yl-benzothiazol-2-yl)-isonicotinamide, 1.23 ml (8.90 mmol) 2-(2-methylaminoethyl)pyridine and 290 mg (0.89 mmol) cesium carbonate in a thick-walled glass pressure tube fitted with a teflon cap was heated at 140° C. for 24 h. The reaction mixture was then cooled to room temperature and poured onto water. The mixture was extracted three times with dichloromethane, and the combined organic phases were washed with saturated brine, dried over sodium sulfate, and concentrated in vacuo. Flash chromatography (0/100–2.5/97.5 methanol/dichlormoethane) followed by trituration in ether afforded 160 mg (71%) N-(4-methoxy-7-morpholin-4-yl-benzothiazol-2-yl)-2-[methyl-(2-pyridin-2-yl-ethyl)-amino]-isonicotinamide as a light yellow crystalline solid. ES-MS m/e (%): 505 (M+H$^+$, 100).

In an analogous manner there were obtained:

EXAMPLE 8

N-(4-Methoxy-7-morpholin-4-yl-benzothiazol-2-yl)-2-(2-pyridin-2-yl-ethylamino)-isonicotinamide From 2-bromo-N-(4-methoxy-7-morpholin-4-yl-benzothiazol-2-yl)-isonicotinamide with cesium carbonate and 2-(2-aminoethyl)-pyridine in NMP. ES-MS m/e (%): 491 (M+H$^+$, 100).

EXAMPLE 9

2-[(2-Methoxy-ethyl)-methyl-amino]-N-(4-methoxy-7-morpholin-4-yl-benzothiazol-2-yl)-isonicotinamide From 2-bromo-N-(4-methoxy-7-mopholin-4-yl-benzothiazol-2-yl)-isonicotinamide with cesium carbonate and N-(2-methoxyethyl)-methylamine. ES-MS m/e (%): 458 (M+H$^+$, 100).

EXAMPLE 10

N-(4-Methoxy-7-morpholin-4-yl-benzothiazol-2-yl)-2-(4-methyl-piperazin-1-yl)-isonicotinamide From 2-bromo-N-(4-methoxy-7-morpholin-4-yl-benzothiazol-2-yl)-isonicotinamide with cesium carbonate and 1-methylpiperazine. ES-MS m/e (%): 469 (M+H$^+$, 100).

EXAMPLE 11

2-(2-Methoxy-ethylamino)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 2-methoxyethylamine. ES-MS m/e (%): 444 (M+H$^+$, 100).

EXAMPLE 12

2-(4-Acetyl-piperazin-1-yl)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 1-acetylpiperazine. ES-MS m/e (%): 519 (M+Na$^+$, 32), 497 (M+H$^+$, 100).

EXAMPLE 13

N-(4-Methoxy-7-morpholin-4-yl-benzothiazol-2-yl)-2-[(pyridin-2-ylmethyl)-amino]-isonicotinamide From 2-bromo-N-(4-methoxy-7-morpholin-4-yl-benzothiazol-2-yl)-isonicotinamide with cesium carbonate and 2-picolylamine. ES-MS m/e (%): 477 (M+H$^+$, 100).

EXAMPLE 14

N-(4-Methoxy-7-morpholin-4-yl-benzothiazol-2-yl)-2-[methyl-(2-piperidin-1-yl-ethyl)-amino]-isonicotinamide From 2-bromo-N-(4-methoxy-7-morpholin-4-yl-benzothiazol-2-yl)-isonicotinamide with cesium carbonate and methyl-(2-piperidin-1-yl-ethyl)-amine. ES-MS m/e (%): 511 (M+H$^+$, 100).

EXAMPLE 15

2-(2-Acetylamino-ethylamino)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and N-acety)-ethylenediamine. ES-MS m/e (%): 493 (M+Na$^+$, 19), 471 (M+H$^+$, 100).

Analogously to Example 1 there were obtained:

EXAMPLE 16

N-(4-Methoxy-7-morpholin-4-yl-benzothiazol-2-yl)-2-(2,2,2-trifluoro-ethoxy)-isonicotinamide From 2-chloro-N-(4-methoxy-7-morpholin-4-yl-benzothiazol-2-yl)-isonicotinamide with sodium hydride and 2,2,2-trifluoroethanol in dioxane and DMF. ES-MS m/e (%): 491 (M+Na$^+$, 81), 469 (M+H$^+$, 100).

EXAMPLE 17

N-(4-Methoxy-7-morpholin-4-yl-benzothiazol-2-yl)-2-[2-(2-oxo-pyrrolidin-1-yl)-ethoxy]-isonicotinamide From 2-chloro-N-(4-methoxy-7-morpholin-4-yl-benzothiazol-2-yl)-isonicotinamide with sodium hydride and 1-(2-hydroxyethyl)-2-pyrrolidone in dioxane. ES-MS m/e (%): 520 (M+Na$^+$, 47), 498 (M+H$^+$, 100). Analogously to Example 7 there were obtained:

EXAMPLE 18

N-(4-Methoxy-7-morpholin-4-yl-benzothiazol-2-yl)-2-(2-morpholin-4-yl-ethylamino)-isonicotinamide From 2-bromo-N-(4-methoxy-7-morpholin-4-yl-benzothiazol-2-yl)-isonicotinamide with cesium carbonate and 4-(2-aminoethyl)-morpholine. ES-MS m/e (%): 499 (M+H$^+$, 100).

EXAMPLE 19

N-(4-Methoxy-7-morpholin-4-yl-benzothiazol-2-yl)-2-(2-piperidin-1-yl-ethylamino)-isonicotinamide From 2-bromo-N-(4-methoxy-7-morpholin-4-yl-benzothiazol-2-yl)-isonicotinamide with cesium carbonate and 1-(2-aminoethyl)-piperidine. ES-MS m/e (%): 497 (M+H$^+$, 100).

EXAMPLE 20

2-[Ethyl-(2-pyridin-2-yl-ethyl)-amino]-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 2-[2-(ethylamino)ethyl]pyridine. ES-MS m/e (%): 519 (M+H$^+$, 100).

EXAMPLE 21

2-[Ethyl-(2-methoxy-ethyl)-amino]-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and N-(2methoxyethyl)ethylamine. ES-MS m/e (%): 472 (M+H$^+$, 100).

EXAMPLE 22

2-(2-Ethoxy-ethylamino)-N-(4-methoxy-7-morpholin-4-yl-benzothiazol-2-yl)-isonicotinamide From 2-bromo-N-(4-methoxy-7-morpholin-4-yl-benzothiazol-2-y)-isonicotinamide with cesium carbonate and 2-ethoxyethylamine. ES-MS m/e (%): 458 (M+H$^+$, 100).

EXAMPLE 23

2-[(2R,6S)-2,6-Dimethyl-morpholin-4-yl]-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and cis-2,6-dimethylmorpholine. ES-MS m/e (%):

EXAMPLE 24

2-Cyclohexyl-N-(4-methoxy-7-morpholin-4-yl-benzothiazol-2-yl)-isonicotinamide a) 2-Cyclohex-1-enyl-N-(4-methoxy-7-morpholin-4-yl-benzothiazol-2-yl)-isonicotinamide To a stirred solution of 400 mg (0.89 mmol) 2-bromo-N-(4-methoxy-7-morpholin-4-yl-benzothiazol-2-yl)-isonicotinamide in 10 ml DMF were added 661 mg (1.78 mmol) tri-n-butyl-cyclohex-1-enyl-stannane, 75 mg, (0.11 mmol) bis(triphenylphosphine)palladium(II) chloride, 140 mg (0.53 mmol) triphenylphosphine, 317 mg (7.48 mmol) lithium chloride and a small spatula-end of 2,6-di-tert-butyl-4-methylphenol. The mixture was heated at 100° C. for 72 h and then concentrated in vacuo. Rough flash chromatography (2/98 methanol/dichloromethane) afforded 520 mg of an orange solid, comprising mainly 2-cyclohex-1-enyl-N-(4-methoxy-7-morpholin-4-yl-benzothiazol-2-yl)-isonicotinamide, which was taken onto the next reaction step without further purification. ES-MS m/e (%): 451 (M+H$^+$, 100).

b) 2-Cyclohexyl-N-(4-methoxy-7-morpholin-4-yl-benzothiazol-2-yl)-isonicotinamide To a stirred solution of 585 mg (theoretically max 1.30 mmol) crude 2-cyclohex-1-enyl-N-(4-methoxy-7-morpholin-4-yl-benzothiazol-2-yl)-isonicotinamide in 5 ml methanol and 10 ml dichloromethane was added 500 mg 10% palladium on charcoal and the mixture was then stirred for 16 h at room temperature under an atmosphere of hydrogen. The mixture was then filtered, washing with dichloromethane, and the filtrate concentrated in vacuo. Flash chromatography (1/19 methanol/dichloromethane) followed by trituration in ether and pentane afforded 125 mg (21%) 2-cyclohexyl-N-(4-methoxy-7-morpholin-4-yl-benzothiazol-2-yl)-isonicotinamide as an off-white crystalline solid.

ES-MS m/e (%): 475 (M+Na$^+$, 26), 453 (M+H$^+$, 100). Analogously to Example 7 there were obtained:

EXAMPLE 25

N-(4-Methoxy-7-morpholin-4-yl-benzothiazol-2-yl)-2-(4-methyl-3-oxo-piperazin-1-yl)-isonicotinamide From 2-bromo-N-(4-methoxy-7-morpholin-4-yl-benzothiazol-2-yl)-isonicotinamide with cesium carbonate and 1-methyl-piperazin-2-one. ES-MS m/e (%): 505 (M+Na$^+$, 31), 483 (M+H$^+$, 100).

EXAMPLE 26

2-Azetidin-1-yl-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and azetidine. ES-MS m/e (%): 426 (M+H$^+$, 100).

EXAMPLE 27

N-(4-Methoxy-7-morpholin-4-yl-benzothiazol-2-yl)-2-(4-methoxy-piperidin-1-yl)-isonicotinamide From 2-bromo-N-(4-methoxy-7-morpholin-4-yl-benzothiazol-2-yl)-isonicotinamide with cesium carbonate and 4-methoxy-piperidine. ES-MS m/e (%): 484 (M+H$^+$, 100).

EXAMPLE 28

N-(4-Methoxy-7-morpholin-4-yl-benzothiazol-2-yl)-2-(3-methoxy-piperidin-1-yl)-isonicotinamide From 2-bromo-N-(4-methoxy-7-morpholin-4-yl-benzothiazol-2-yl)-isonicotinamide with cesium carbonate and 3-methoxy-piperidine. ES-MS m/e (%): 484 (M+H$^+$, 100).

EXAMPLE 29

2-(4-Ethyl-3-oxo-piperazin-1-yl)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 1-ethyl-piperazin-2-one. ES-MS m/e (%):519 (M+Na$^+$, 28), 497 (M+H$^{30}$, 100).

Analogously to Example 24 there was obtained:

EXAMPLE 30

N-(4-Methoxy-7-morpholin-4-yl-benzothiazol-2-yl)-2-(tetrahydro-pyran-4-yl)-isonicotinamide From 2-bromo-N-(4-methoxy-7-morpholin-4-yl-benzothiazol-2-yl)-isonicotinamide with tri-n-butyl-(3,6-dihydro-2H-pyrin-4-yl)-stannane, bis(triphenylphosphine)palladium(II) chloride, triphenylphosphine, lithium chloride and 2,6-di-tert-butyl-4-methylphenol in DMF. Then hydrogenation using palladium on charcoal in methanol and dichloromethane. ES-MS m/e (%): 477 (M+Na+, 16), 455 (M+H$^+$, 100).

Analogously to Example 7 there were obtained:

EXAMPLE 31

N-(4-Methoxy-7-morpholin-4-yl-benzothiazol-2-yl)-2-{(1S,4S)-2-oxa-5-aza-bicyclo[2.2.1]hept-5-yl}-isonicotinamide From 2-bromo-N-(4-methoxy-7-morpholin-4-yl-benzothiazol-2-yl)-isonicotinamide with cesium carbonate and (1S,4S)-(+)-2-aza-5-oxabicyclol 2.2.1]heptane hydrochloride. ES-MS m/e (%): 590 (M+Na$^+$, 17), 468 (M+H$^+$, 100).

EXAMPLE 32

2-(3-hydroxy-piperidin-1-yl)-N-(4-Methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 3-hydroxy-piperidine. ES-MS m/e (%): 470 (M+H$^+$, 100).

EXAMPLE 33

2-(4-Hydroxy-piperidin-1-yl)-N-(4-Methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 4-hydroxy-piperidine. ES-MS m/e (%): 470 (M+H$^+$, 100).

EXAMPLE 34

6-Ethoxy-N-(4-methoxy-7-morpholin-4-yl-benzothiazol-2-yl)-nicotinamide a) 6-Chloro-N-(4-methoxy-7-morpholin-4-yl-benzothiazol-2-yl)-nicotinamide To a stirred solution of 1.89 g (7.54 mmol) 6-chloro-nicotinic acid in 20 ml THF were added 2.87 g (7.54 mmol) HATU and 1.28 ml (7.54 mmol) N-ethyldiisopropylamine and stirring continued at room temperature for 30 minutes. A solution of 2.00 g (7.54 mmol) 4-methoxy-7-morpholin-4-yl-benzothiazol-2-ylamine in 20 ml dioxane and 4 ml DMF was then added and stirring continued at room temperature for 16 h. The reaction mixture was then poured into 350 ml water and the mixture stirred for 30 min. The resulting crystals were collected by filtration, washed with methanol and then with ether, and dried in vacuo to afford 3.03 g (99%) 6-chloro-N-(4-methoxy-7-morpholin-4-yl-benzothiazol-2-yl)-nicotinamide as a yellow crystalline solid. ES-MS m/e (%): 429 (M{$^{37}$Cl}+Na$^+$, 15), 427 (M{$^{35}$Cl}+Na$^+$, 38). 407 (M{$^{37}$Cl}+H$^+$, 40), 405 (M{$^{31}$Cl}+H$^+$, 100)

b) 6-Ethoxy-N-(4-methoxy-7-morpholin-4-yl-benzothiazol-2-yl)-nicotinamide

To a stirred solution of 0.24 ml (4.94 mmol) ethanol in 5 ml dioxane at room temperature was added 270 mg (6.18 mmol) sodium hydride (55% dispersion in mineral oil) and the mixture heated at 50° C. for 30 min. 500 mg (1.23 mmol) 6-chloro-N-(4-methoxy-7-morpholin-4-yl-benzothiazol-2- yl)-nicotinamide was then added and the mixture heated at 80° C. for 16 h. The reaction mixture was then cooled to room temperature and poured onto water. The mixture was extracted three times with dichloromethane, and the combined organic phases were dried over sodium sulfate and concentrated in vacuo. Flash chromatography (1/99 methanol/dichloromethane) followed by trituration in ether afforded 270 mg (53%) 6-ethoxy-N-(4-methoxy-7-morpholin-4-yl-benzothiazol-2-yl)-nicotinamide as a white crystalline solid. ES-MS m/e (%): 437 (M+Na$^+$, 26), 415 (M+H$^+$, 100).

In an analogous manner there was obtained:

EXAMPLE 35

6-Methoxy-N-(4-methoxy-7-morpholin-4-yl-benzothiazol-2-yl)-nicotinamide

From 6-chloro-N-(4-methoxy-7-morpholin-4-yl-benzothiazol-2-yl)-nicotinamide with sodium hydride and methanol in dioxane and DMF. ES-MS m/e (%): 423 (M+Na$^+$, 15), 401 (M+H$^+$, 100).

EXAMPLE 36

6-(4-Acetyl-piperazin-1-yl)-N-(4-methoxy-7-morpholin-4-yl-benzothiazol-2-yl)-nicotinamide A stirred suspension of 200 mg (0.49 mmol) 6-chloro-N-(4-methoxy-7-morpholin-4-yl-benzothiazol-2-yl)-nicotinamide, 2.53 g (19.8 mmol) 1-acetylpiperazine and 290 mg (0.89 mmol) cesium carbonate in 4 ml NMP in a thick-walled glass pressure tube fitted with a teflon cap was heated at 120° C. for 24 h. The reaction mixture was then cooled to room temperature and poured onto water. The mixture was extracted three times with dichloromethane, and the combined organic phases were washed with saturated brine, dried over sodium sulfate, and concentrated in vacuo. Flash chromatography (0/99–4/96 methanol/dichlormoethane) followed by trituration in ether afforded 77 mg (31%) 6-(4-acetyl-piperazin-1-yl)-N-(4-methoxy-7-morpholin-4-yl-benzothiazol-2-yl)-nicotinamide as a white crystalline solid. ES-MS m/e (%): 519 (M+Na$^+$, 26), 417 (M+H$^+$, 100).

Analogously to Example 34 there was obtained:

EXAMPLE 37

6-(2-Methoxy-ethoxy)-N-(4-methoxy-7-morpholin-4-yl-benzothiazol-2-yl)-nicotinamide From 6-chloro-N-(4-methoxy-7-morpholin-4-yl-benzothiazol-2-yl)-nicotinamide with sodium hydride and 2-methoxyethanol in dioxane and DMF. ES-MS m/e (%): 467 (M+Na$^+$, 24), 445 (M+H$^+$, 100).

Analogously to Example 36 there were obtained:

EXAMPLE 38

N-(4-Methoxy-7-morpholin-4-yl-benzothiazol-2-yl)-6-(4-methyl-piperazin-1-yl)-nicotinamide From 6-chloro-N-(4-methoxy-7-morpholin-4-yl-benzothiazol-2-yl)-nicotinamide with cesium carbonate and 1-methyl-piperazine in NMP. ES-MS m/e (%): 469 (M+H$^+$, 100).

EXAMPLE 39

6-[(2R,6S)-2,6-Dimethyl-morpholin-4-yl]-N-(4-methoxy-7-morpholin-4-yl-benzothiazol-2-yl)-nicotinamide From 6-chloro-N-(4-methoxy-7-morpholin-4-yl-benzothiazol-2-yl)-nicotinamide with cesium carbonate and cis-2,6-dimethyl-morpholine in NMP. ES-MS m/e (%): 506 (M+Na$^+$, 31), 484 (M+H$^+$, 100).

EXAMPLE 40

N-(4-Methoxy-7-morpholin-4-yl-benzothiazol-2-yl)-6-[(pyridin-2-ylmethyl)-amino]-nicotinamide From 6-chloro-N-(4-methoxy-7-morpholin-4-yl-benzothiazo-2-yl)-nicotinamide with cesium carbonate and 2-picolylamine. ES-MS m/e (%): 499 (M+Na$^+$, 19), 477 (M+H$^+$, 100).

EXAMPLE 41

6-(2-Methoxy-ethylamino)-N-(4-methoxy-7-morpholin-4-yl-benzothiazol-2-yl)-nicotinamide From 6-chloro-N-(4-methoxy-7-morpholin-4-yl-benzothiazol-2-yl)-nicotinamide with cesium carbonate and 2-methoxyethylamine. ES-MS m/e (%): 444 (M+H$^+$, 100).

Analogously to Example 34 there were obtained:

EXAMPLE 42

N-(4-Methoxy-7-morpholin-4-yl-benzothiazol-2-y)-6-propoxy-nicotinamide

From 6-chloro-N-(4-methoxy-7-morpholin-4-yl-benzothiazol-2-yl)-nicotinamide with sodium hydride and propanol in dioxane and DMF. ES-MS m/e (%): 429 (M+H$^+$, 100).

EXAMPLE 43

6-Butoxy-N-(4-methoxy-7-morpholin-4-yl-benzothiazol-2-yl)-nicotinamide

From 6-chloro-N-(4-methoxy-7-mopholin-4-yl-benzothiazol-2-yl)-nicotinamide with sodium hydride and butanol in dioxane and DMF. ES-MS m/e (%): 465 (M+Na$^+$, 40), 443 (M+H$^+$, 100).

EXAMPLE 44

6-Isopropoxy-N-(4-methoxy-7-morpholin-4-yl-benzothiazol-2-yl)-nicotinamide

From 6-chloro-N-(4-methoxy-7-morpholin-4-yl-benzothiazol-2-yl)-nicotinamide with sodium hydride and isopropanol in dioxane and DMF. ES-MS m/e (%): 451 (M+Na$^+$, 20), 429 (M+H$^+$, 100).

EXAMPLE 45

6-Cyclohexyloxy-N-(4-methoxy-7-morpholin-4-yl-benzothiazol-2-yl)-nicotinamide

From 6-chloro-N-(4-methoxy-7-morpholin-4-yl-benzothiazol-2-yl)-nicotinamide with sodium hydride and cyclohexanol in dioxane and DMF. ES-MS m/e (%): 491 (M+Na$^+$, 24), 469 (M+H$^+$, 100).

EXAMPLE 46

2-{[(2-Methoxy-ethyl)-methyl-amino]-methyl}-N-(4-methoxy-7-morpholin-4-yl-benzothiazol-2-yl)-isonicotinamide 2-Chloromethyl-N-(4-methoxy-7-morpholin-4-yl-benzothiazol-2-yl)-isonicotinamide (240 mg, 0.55 mmol) is dissolved in N-(2-methoxyethyl)-methylamine (1.0 g, 12 mmol) and the mixture heated to 60° C. for 1 h. The volatile components are removed in vacuo and the residue chromatographed over $SiO_2$ eluting with dichloromethane/methanol 19/1. The title compound was obtained as yellow crystals (170 mg, 71% yield). MS: m/e=472(M+H+). Following the general method of example 46 the compounds of examples 47–62 were prepared.

EXAMPLE 47

2-[(2-Methoxy-ethylamino)-methyl]-N-(4-methoxy-7-morpholin-4-yl-benzothiazol-2-yl)-isonicotinamide Using 2-methoxy-ethylamine the title compound was prepared as yellow crystals (68% yield). MS: m/e=458 (M+H$^+$).

EXAMPLE 48

2-{[Ethyl-(2-methoxy-ethyl)-amino]-methyl}-N-(4-methoxy-7-morpholin-4-yl-benzothiazol-2-yl)-isonicotinamide Using N-ethyl-(2-methoxy-ethyl)-amine the title compound was prepared as off-white solid (76%) yield). MS: m/e=486 (M+H$^+$).

EXAMPLE 49

2-{[(2-Ethoxy-ethyl)-ethyl-amino]-methyl}-N-(4-methoxy-7-morpholin-4-yl-benzothiazol-2-yl)-isonicotinamide Using N-(2-ethoxy-ethyl)-ethyl-amine the title Compound was prepared as brown solid (67% yield). MS: m/e=500 (M+H$^+$).

EXAMPLE 50

2-[(2-Ethoxy-ethylamino)-methyl]-N-(4-methoxy-7-morpholin-4-yl-benzothiazol-2-yl)-isonicotinamide Using 2-ethoxy-ethylamine the title compound was prepared as yellow solid (44% yield). MS: m/e=472 (M+H$^+$).

EXAMPLE 51

2-[(Butyl-methyl-amino)-methyl]-N-(4-methoxy-7-morpholin-4-yl-benzothiazol-2-yl)-isonicotinamide Using N-butyl-methylamine the title compound was prepared as yellow solid (70% yield). MS: m/e=470 (M+H$^+$).

EXAMPLE 52

2-Butylaminomethyl-N-(4-methoxy-7-morpholin-4-yl-benzothiazol-2-yl)-isonicotinamide Using butylamine the title compound was prepared as yellow solid (58% yield). MS: m/e=456 (M+H$^+$).

EXAMPLE 53

2-Diethylaminomethyl-N-(4-methoxy-7-morpholin-4-yl-benzothiazol-2-yl)-isonicotinamide Using diethylamine the title Compound was prepared as light yellow solid (55% yield). MS: m/e=456 (M+H$^+$).

EXAMPLE 54

N-(4-Methoxy-7-morpholin-4-yl-benzothiazol-2-yl)-2-pyrrolidin-1-ylmethyl-isonicotinamide Using pyrrolidine the title compound was prepared as yellow crystals (63% yield). MS: m/e=454(M+H$^+$).

EXAMPLE 55

N-(4-Methoxy-7-morpholin-4-yl-benzothiazol-2-yl)-2-piperidin-1-ylmethyl-isonicotinamide Using piperidine the title compound was prepared as off-white solid (56% yield). MS: m/e=468 (M+H$^+$).

EXAMPLE 56

N-(4-Methoxy-7-morpholin-4-yl-benzothiazol-2-yl)-2-morpholin-4-ylmethyl-isonicotinamide Using morpholine the title compound was prepared as light brown solid (76% yield). MS: m/e=470 (M+H$^+$).

EXAMPLE 57

N-(4-Methoxy-7-morpholin-4-yl-benzothiazol-2-yl)-2-(4-methoxy-piperidin-1-ylmethyl)-isonicotinamide Using 4-methoxy-piperidine the title compound was prepared as light brown solid (99% yield). MS: m/e=498 (M+H$^+$).

EXAMPLE 58

N-(4-Methoxy-7-morpholin-4-yl-benzothiazol-2-yl)-2-methylaminomethyl-isonicotinamide Using methylamine the title compound was prepared as yellow crystals (30% yield). MS: m/e=414 (M+H$^+$).

EXAMPLE 59

2-Ethylaminomethyl-N-(4-methoxy-7-morpholin-4-yl-benzothiazol-2-yl)-isonicotinamide Using ethylamine the title compound was prepared as yellow crystals (70% yield). MS: m/e=428 (M+H$^+$).

EXAMPLE 60

2-[(Cyclopropylmethyl-amino)-methyl]-N-(4-methoxy-7-morpholin-4-yl-benzothiazol-2-yl)-isonicotinamide Using C-cyclopropyl-methylamine the title compound was prepared as yellow crystals (70% yield). MS: m/e=454 (M+H$^+$).

EXAMPLE 61

2-Azetidin-1-yl-methyl-N-(4-methoxy-7-morpholin-4-yl-benzothiazol-2-yl)-isonicotinamide Using azetidine the title compound was prepared as yellow crystals (24% yield). MS: m/e=440 (M+H$^+$).

EXAMPLE 62

4-{[4-(4-Methoxy-7-morpholin-4-yl-benzothiazol-2-yl-carbamoyl)-pyridin-2-yl-methyl]-amino}-butyric Acid tert-Butyl Ester Using 4-amino-butyric acid tert-butyl ester in 10 parts tetrahydrofurane the title compound was prepared as light brown solid (43%) yield). MS: m/e=542 (M+H$^+$).

EXAMPLE 63

4-{[4-(4-Methoxy-7-morpholin-4-yl-benzothiazol-2-yl-carbamoyl)-pyridin-2-yl-methyl]-amino}-butyric Acid Treatment of 4-{[4-(4-methoxy-7-morpholin-4-yl-benzothiazol-2-yl-carbamoyl)-pyridin-2-yl-methyl]- amino}-butyric acid tert-butyl ester (214 mg, 0.40 mmol) with trifluoroacetic acid (1§.0 ml, 13 mmol) yields the title compound in >95% yield as light brown solid. MS: m/e=486 (M+H⁺).

EXAMPLE 64

N-(4-Methoxy-7-morpholin-4-yl-benzothiazol-2-yl)-2-(2-oxo-pyrrolidin-1-yl-methyl)-isonicotinamide To 2-pyrrolidinone (2.0 ml, 26 mmol) are added sodium hydride (45 mg, 1.1 mmol, 60% in mineral oil) followed after 15 min. by 2-chloromethyl-N-(4-methoxy-7-morpholin-4-yl-benzothiazol-2-yl)-isoinicotinamide (210 mg, 0.50 mmol) and the remaining, mixture is stirred for 3 h at 80° C. The mixture is the treated with water (15 ml) and evaporated to dryness. Flash chromatography (SiO₂, eluent: dichloromethane/methanol 19:1) and subsequent recrystallization from dichloromethane/ethanol afforded the title compound as yellow crystals (129 mg, 55% yield). MS: m/e=468 (M+H⁺).

EXAMPLE 65

[4-(4-Methoxy-7-morpholin-4-yl-benzothiazol-2-yl-carbamoyl)-pyridin-2-ylmethyl]-methyl-carbamic Acid Methyl Ester A solution of N-(4-methoxy-7-morpholin-4-yl-benzothiazol-2-yl)-2-methylaminomethyl-isonicotinamide (180 mg, 0.44 mmol) in tetrahydrofurane(15 ml) is subsequently treated with pyridine(52 µl, 0.65 mmol) and methyl chloroformate (43 µl, 0.57 mmol)and stirred at ambient temperature for 15 h. Additional pyridine (25 µl, 0.31 mmol) and methylchloroformate (20 µl, 0.26 mmol) are added and the mixture stirred for another hour. Saturated sodium hydrogen carbonate (15 ml) is added and the mixture extracted four times with ethyl acetate. The combined organic ohases are dried with magnesium sulfate and evaporated to dryness. Flash chromatography (SiO₂, eluent: dichloromethane/methanol 19:1) afforded the title compound as yellow crystals (115 mg, 56% yield). MS: m/e=472 (M+H⁺).

EXAMPLE 66

2-(2-Methoxy-ethoxymethyl)-N-(4-methoxy-7-morpholin-4-yl-benzothiazol-2-yl)-isonicotinamide 2-Methoxyethanol (2.6 ml, 48 mmol) is treated at 0° C. with sodium hydride (38 mg, 0.95 mmol, 60% in mineral oil) and the remaining solution allowed to warm to ambient temperature over 1 h. N-(4-Methoxy-7-morpholin-4-yl-benzothiazol-2-yl)-2-methylaminomethyl-isonicotinamide (200 mg, 0.48 mmol, dissolved in tetrahydrofurane (2.0 ml), is added and the mixture stirred at 80° C. for 15 h. The mixture is then evaporated to dryness, treated with saturated sodium carbonate (20 ml) and extracted four times with each 20 ml dichloromethane. The combined organic phases are dryed and evaporated. Flash chromatography (SiO₂, eluent: dichloromethane/methanol 20:0 to 19:1) afforded the title compound as light yellow crystals (104 mg, 48% yield). MS: m/e=459 (M+H⁺).

EXAMPLE 67

2-Methoxymethyl-N-(4-methoxy-7-morpholin-4-yl-benzothiazol-2-yl)-isonicotinamide N-(4-Methoxy-7-morpholin-4-yl-benzothiazol-2-yl)-2-methylaminomethyl-isonicotinamide (200 mg, 0.48 mmol, dissolved in tetrahydrofurane (5.0 ml), is treated with sodium methoxide (81 mg, 1.4 mmol) at 0° C. and the mixture heated to 50° C. for 15 h. The mixture is quenched with saturated sodium carbonate (4.0 ml), extracted four times with each 15 ml dichloromethane and the combined organic phases dryed and evaporated. Flash chromatography (first SiO₂, eluent: dichloromethane/methanol 0 to 5% and second dichloromethane/ethyl acetae 30% to 60%) afforded the title compound as light yellow crystals (49 mg, 25% yield). MS: m/e=415 (M+H⁺).

Preparation of intermediates for examples 46 to 67.

EXAMPLE 68 (INTERMEDIATE)

2-Chloromethyl-N-(4-methoxy-7-morpholin-4-yl-benzothiazol-2-yl)-isonicotinamide

To a solution of 4-methoxy-7-morpholin-4-yl-benzothiazol-2-yl-amine (2.3 g, 8.7 mmol) in tetrahydrofurane (80 ml) is added N-ethyldiisopropylamine (6.0 ml, 35 mmol) and the solution cooled to 0° C. 2-chloromethyl-isonicotinoyl chloride (2.4 g, 10.5 mmol), dissolved in tetrahydrofurane (50 ml), is added over 15 minutes and the mixture heated to 70° C. for 1 h. After evaporation of the volatile components, the residue was disolved in ethyl acetate and water, filtered and the residue combined with the dryed and evaporated organic phase. Recrystallization from dichloromethane/ethyl acetate afforded the title compound as light brown solid (2.9 g, 81% yield). MS: m/e=420(M+H⁺).

EXAMPLE 69

(2-Chloromethyl-isonicotinoyl Chloride (Intermediate)

Hydrolysis of 2-chloromethyl-isoticotinic acid methyl ester (derived as described by Scopes et al., *J. Med. Chem.* 1992, 35, 492) with LiOH in MeOH and water and subsequent acid chloride formation with oxalyl chloride/dimethylformamide in dichloromethane gave the title compound as light brown oil in about 80% yield, which was used without further purification.

EXAMPLE 70

N-(4-Methoxy-7-piperidin-1-yl-benzothiazol-2-yl)-2-pyrrolidin-1-yl-methyl-isonicotinamide Using 2-chloromethyl-N-(4-methoxy-7-piperidin-1-yl-benzothiazol-2-yl)-isonicotinamide and pyrrolidine the title compound was prepared as described for example 46 as light yellow crystals (67% yield). MS: m/e=452 (M+H+).

EXAMPLE 71

N-(4-Methoxy-7-piperidin-1-yl-benzothiazol-2-yl)-2-morpholin-4-yl-methyl-isonicotinamide Using 2-chloromethyl-N-(4-methoxy-7-piperidin-1-yl-benzothiazol-2-yl)-isonicotinamide and morpholine the title compound was prepared as described for example 1 as light yellow crystals (54% yield). MS: m/e=468 (M+H+).

Preparation of intermediates for examples 70 and 71.

EXAMPLE 72

2-Chloromethyl-N-(4-methoxy-7-piperidin-1-yl-benzothiazol-2-yl)-isonicotinamide (Intermediate)

Using 4-methoxy-7-piperidin-1-yl-benzothiazol-2-yl-amine the title compound was prepared as described for 2-chloromethyl-N-(4-methoxy-7-morpholin-4-yl-benzothiazol-2-yl)-isonicotinamide as yellow crystals (70% yield). MS: m/e=417 (M+H⁺).

EXAMPLE 73

2-(1,1-Dioxo-1l6-thiomorpholin-4-yl)-N-(4-methoxy-7-morpholin-4-yl-benzothiazol-2-yl)-isonicotinamide a) N-(4-Methoxy-7-morpholin-4-yl-benzothiazol-2-yl)-2-thiomorpholin-4-yl-isonicotinamide A stirred suspension of 500 mg (1.11 mmol) 2-bromo-N-(4-methoxy-7-morpholin-4-yl-benzothiazol-2-yl)-isonicotinamide. 1.5 g (11.1 mmol) thiomorpholine and 725 mg (2.23 mmol) cesium carbonate in a thick-walled glass pressure tube fitted with a teflon cap was heated at 140° C. for 48 h. The reaction mixture was then cooled to room temperature and poured onto water. The mixture was extracted three times with ethyl acetate, and the combined organic phases were washed with saturated brine, dried over sodium sulfate, and concentrated in vacuo. Flash chromatography (1/99 methanol/dichloromethane) followed by trituration in ether/ethyl acetate/hexane afforded 290 mg (55%) N-(4-methoxy-7-morpholin-4-yl-benzothiazol-2-yl)-2-thiomorpholin-4-yl-isonicotinamide as an off-white crystalline solid. ES-MS m/e (%)): 472 (M+H⁺, 100).

b) 2-(1,1-Dioxo-1l6-thiomorpholin-4-yl)-N-(4-methoxy-7-morpholin-4-yl-benzothiazol-2-yl)-isonicotinamide To a stirred solution of 500 mg (1.06 mmol) N-(4-methoxy-7-morpholin-4-yl-benzothiazol-2-yl)-2-thiomorpholin-4-yl-isonicotinamide in 5 ml methanol and 5 ml dichloromethane at room temperature was added 652 mg (1.06 mmol) oxone and stirring was continued for 60 h. The reaction was then quenched by careful addition of 5 ml saturated aqueous sodium hydrogensulfite solution and the pH of the resulting mixture was then adjusted to pH by addition of aqueous sodium bicarbonate solution. The mixture was extracted three times with dichloromethane and the combined organic phases were dried over sodium sulfate and concentrated in vacuo. Flash chromatography (0.5/99.5 methanol/dichloromethane) followed by trituration in ether afforded 90 mg (17%) 2-(1,1-Dioxo-1l6-thiomorpholin-4-yl)-N-(4-methoxy-7-morpholin-4-yl-benzothiazol-2-yl)-isonicotinamide as a yellow crystalline solid. ES-MS m/e (%): 504 (M+H⁺, 100).

Analogously to Example 7 there were obtained:

EXAMPLE 74

2-(3-Hydroxy-azetidin-1-yl)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and azetidin-3-ol in NMP. ES-MS m/e (%): 442 (M+H⁺, 100).

EXAMPLE 75

2-(3-Methoxy-azetidin-1-yl)-N-(4-methoxy-7-morpholin-4-yl-benzothiazol-2-yl)-isonicotinamide From 2-bromo-N-(4-methoxy-7-mopholin-4-yl-benzothiazol-2-yl)-isonicotinamide with cesium carbonate and 3-methoxy-azetidine hydrochloride in NMP. ES-MS m/e (%): 456 (M+H⁺, 100).

EXAMPLE 76

2-(3-Ethoxy-azetidin-1-yl)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 3-ethoxy-azetidine hydrochloride in NMP. ES-MS m/e (%): 470 (M+H⁺, 100).

Analogously to Example 1 there were obtained:

EXAMPLE 77

2-Isopropoxy-N-(4-methoxy-7-morpholin-4-yl-benzothiazol-2-yl)-isonicotinamide

From 2-bromo-N-(4-methoxy-7-morpholin-4-yl-benzothiazol-2-yl)-isonicotinamide with sodium hydride and isopropanol in dioxane and DMF. ES-MS m/e (%): 429 (M+H⁺, 100).

EXAMPLE 78

2-Cyclohexyloxy-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with sodium hydride and cyclohexanol in dioxane and DMF. ES-MS m/e (%): 469 (M+H⁺, 100).

Analogously to Example 7 there was obtained:

EXAMPLE 79

2-Cyclohexylamino-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and cyclohexylamine in NMP. ES-MS m/e (%): 468 (M+H⁺, 100).

Analogously to Example 1 there were obtained:

EXAMPLE 80

N-(4-Methoxy-7-morpholin-4-yl-benzothiazol-2-yl)-2-methylsulfanyl-isonicotinamide From 2-bromo-N-(4-methoxy-7-morpholin-4-yl-benzothiazol-2-yl)-isonicotinamide with sodium methanethiolate in dioxane and DMF. ES-MS m/e (%): 417 (M+H⁺, 100).

EXAMPLE 81

2-Ethylsulfanyl-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with sodium ethanethiolate in dioxane and DMF. ES-MS m/e (%): 431 (M+H⁺, 100).

EXAMPLE 82

2-Butylsulfanyl-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with sodium hydride and butanethiol in dioxane and DMF. ES-MS m/e (%): 459 (M+H⁺, 100).

Analogously to Example 7 there was obtained:

EXAMPLE 83

2-Benzylamino-N-(4-methoxy-7-morpholin-4-yl-benzothiazol-2-yl)-isonicotinamide

From 2-bromo-N-(4-methoxy-7-morpholin-4-yl-benzothiazol-2-yl)-isonicotinamide with cesium carbonate and benzylamine. ES-MS m/e (%): 476 (M+H⁺, 100).

Analogously to Example 1 there were obtained:

EXAMPLE 84

2-Isobutoxy-N-(4-methoxy-7-morpholin-4-yl-benzothiazol-2-yl)-isonicotinamide

From 2-bromo-N-(4-methoxy-7-morpholin-4-yl-benzothiazol-2-yl)-isonicotinamide with sodium hydride and 2-methyl-propanol in dioxane and DMF. ES-MS m/e (%): 443 (M+H$^+$, 100).

EXAMPLE 85

2-Cyclopentyloxy-N-(4-methoxy-7-morpholin-4-yl-benzothiazol-2-yl)-isonicotinamide From 2-bromo-N-(4-methoxy-7-morpholin-4-y2-benzothiazol-2-yl)-isonicotinamide with sodium hydride and cyclopentanol in dioxane and DMF. ES-MS m/e (%): 455 (M+H$^+$, 100).

EXAMPLE 86

2-(2-Dimethylamino-ethoxy)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with sodium hydride and 2-dimethylaminoethanol in dioxane and DMF. ES-MS m/e (%): 458 (M+H$^+$, 100).

EXAMPLE 87

N-(4-Methoxy-7-morpholin-4-yl-benzothiazol-2-yl)-2-(2-morpholin-4-yl-ethoxy)-isonicotinamide From 2-bromo-N-(4-methoxy-7-morpholin-4-yl-benzothiazol-2-yl)-isonicotinamide with sodium hydride and N-(2-hydroxyethyl)morpholine in dioxane and DMF. ES-MS m/e (%): 500 (M+H$^+$, 100).

Analogously to Example 7 there were obtained:

EXAMPLE 88

2-(2-Dimethylamino-ethylamino)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and 2-dimethylaminoethylamine. ES-MS m/e (%): 457 (M+H$^{+b,\ 100}$).

EXAMPLE 89

2-Cyclopentylamino-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and cyclopentylamine. ES-MS m/e (%): 454 (M+H$^+$, 100).

EXAMPLE 90

2-Cyclobutylamino-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and cyclobutylamine. ES-MS m/e (%): 440 (M+H$^+$, 100).

Analogously to Example 36 there was obtained:

EXAMPLE 91

6-[Ethyl-(2-methoxy-ethyl)-amino]-N-(4-methoxy-7-morpholin-4-yl-benzothiazol-2-yl)-nicotinamide From 6-chloro-N-(4-methoxy-7-morpholin-4-yl-benzothiazol-2-yl)-nicotinamide with cesium carbonate and N-(2-methoxyethyl)ethylamine. ES-MS m/e (%): 472 (M+H$^+$, 100).

Analogously to Example 1 there was obtained:

EXAMPLE 92

2-(2-Acetylamino-ethoxy)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with sodium hydride and N-acetylethiazolamine in dioxane. ES-MS m/e (%): 472 (M+H$^+$, 100).

Analogously to Example 7 there were obtained:

EXAMPLE 93

N-(4-Methoxy-7-morpholin-4-yl-benzothiazol-2-yl)-2-propylamino-isonicotinamide

From 2-bromo-N-(4-methoxy-7-morpholin-4-yl-benzothiazol-2-yl)-isonicotinamide with cesium carbonate and propylamine. ES-MS m/e (%): 428 (M+H$^+$, 100).

EXAMPLE 94

N-(4-Methoxy-7-morpholin-4-yl-benzothiazol-2-yl)-2-(methyl-propyl-amino)-isonicotinamide From 2-bromo-N-(4-methoxy-7-morpholin-4-yl-benzothiazol-2-yl)-isonicotinamide with cesium carbonate and N-methyl-N-propylamine in DMF. ES-MS m/e (%): 442 (M+H$^+$, 100).

EXAMPLE 95

2-(Cyclohexyl-methyl-amino)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and N-methylcyclohexylamine. ES-MS m/e (%): 482 (M+H$^+$, 100).

EXAMPLE 96

2-(Benzyl-methyl-amino)-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and N-methylbenzylamine. ES-MS m/e (%): 490 (M+H$^+$, 100).

EXAMPLE 97

N-(4-Methoxy-7-morpholin-4-yl-benzothiazol-2-yl)-2-(methyl-phenethyl-amino)-isonicotinamide From 2-bromo-N-(4-methoxy-7-morpholin-4-yl-benzothiazol-2-yl)-isonicotinamide with cesium carbonate and N-methyl-2-phenylethylamine. ES-MS m/e (%): 504 (M+H$^+$, 100).

EXAMPLE 98

N-(4-Methoxy-7-morpholin-4-yl-benzothiazol-2-yl)-2-phenethylamino-isonicotinamide From 2-bromo-N-(4-methoxy-7-morpholin-4-yl-benzothiazol-2-yl)-isonicotinamide with cesium carbonate and phenylethylamine. ES-MS m/e (%): 490 (M+H$^+$, 100).

EXAMPLE 99

2-[(2-Dimethylamino-ethyl)-methyl-amino]-N-(4-methoxy-7-morpholin-4-yl-benzothiazol-2-yl)-isonicotinamide From 2-bromo-N-(4-methoxy-7-morpholin-4-yl-benzothiazol-2-yl)-isonicotinamide with cesium carbonate and N,N,N'-trimethylethylenediamine. ES-MS m/e (%): 471 (M+H$^+$, 100).

EXAMPLE 100

N-(4-Methoxy-7-piperidin-1-yl-benzothiazol-2-yl)-2-(4-methyl-piperazin-1-yl)-isonicotinamide From 2-bromo-N-(4-methoxy-7-piperidin-1-yl-benzothiazol-2-yl)-isonicotinamide with cesium carbonate and N-methylpiperazine. ES-MS m/e (%): 467 (M+H$^+$, 100).

Analogously to Example 1 there was obtained:

EXAMPLE 101

2-Methoxy-N-(4-methoxy-7-phenyl-benzothiazol-2-yl)-isonicotinamide

From 2-bromo-N-(4-methoxy-7-phenyl-benzothiazol-2-yl)-isonicotinamide with sodium hydride and methanol in dioxane. ES-MS m/e (%): 392 (M+H$^+$, 100).

The following examples were made from intermediate 68(2-chloromethyl-N-(4-methoxy-7-morpholin-4-yl-benzothiazol-2-yl)-isonicotinamide) in the manner for example 46:

EXAMPLE 102

2-(4-Hydroxy-piperidin-1-yl-methyl)-N-(4-methoxy-7-morpholin-4-yl-benzothiazol-2-yl)-isonicotinamide Using 4-hydroxy-piperidine the title compound was prepared as yellow crystals (68% yield), mp 125° C. MS: m/e=484 (M+H$^+$).

EXAMPLE 103

2-Ethylsulfanylmethyl-N-(4-methoxy-7-morpholin-4-yl-benzothiazol-2-yl)-isonicotinamide Using ethanethiol and N-ethyl-diisopropylamine (1.1 eq) and sodium methanolate (1 eq), the title compound was prepared as light brown crystals (41% yield), mp 158–159° C. MS: m/e=445 (M+H$^+$).

EXAMPLE 104

2-{[(2-Ethoxy-ethyl)-methyl-amino]-methyl}-N-(4-methoxy-7-morpholin-4-yl-benzothiazol-2-yl)-isonicotinamide Using N-(2-ethoxy)-methylethylamine the title compound was prepared as yellow crystals (41% yield), mp 159–160° C. MS: m/e=486 (M+H$^+$).

EXAMPLE 105

(S)-2-(2-Methoxymethyl-pyrrolidin-1-ylmethyl)-N-(4-methoxy-7-morpholin-4-yl-benzothiazol-2-yl)-isonicotinamide Using (S)-2-methoxymethyl)pyrrolidine the title compound was prepared as yellow solid (45% yield), mp 110–113° C. MS: m/e=498 (M+H$^+$).

EXAMPLE 106

(S)-2-(3-Methoxymethyl-pyrrolidin-1-ylmethyl)-N-(4-methoxy-7-morpholin-4-yl-benzothiazol-2-yl)-isonicotinamide Using (S)-3-methoxymethyl)pyrrolidine the title compound was prepared as light-yellow solid (30% yield), mp 93–96° C. MS: m/e=498 (M+H$^+$).

EXAMPLE 107

N-(4-Methoxy-7-morpholin-4-yl-benzothiazol-2-yl)-2-(2-methyl-imidazol-1-ylmethyl)-isonicotinamide Using 2-methyl-imidazole and dioxane the title compound was prepared as light-brown solid (87% yield), mp 264–265° C. MS: m/e=465 (M+H$^+$).

EXAMPLE 108

2-[(Acetyl-methyl-amino)-methyl]-N-(4-methoxy-7-morpholin-4-yl-benzothiazol-2-yl)-isonicotinamide N-(4-Methoxy-7-morpholin-4-yl-benzothiazol-2-yl)-2-methylaminomethyl-isonicotinamide (207 mg, 0.5 mmol) is dissolved in dichloromethane (10 ml) and treated with pyridine (0.07 ml, 0.85 mmol) and acetyl chloride (0.05 ml, 0.7 mmol) and stirred for 16 h at ambient temperature. Saturated aqueous sodium hydrogen carbonate (10 ml) is added, the layers are separated and the aqueous phase extracted twice with each 10 ml dichloromethane. The combined organic phases are dried with magnesium sulfate and evaporated. Recrystallization from ethyl acetate afforded the title compound as light-yellow solid (80% yield), mp 228–230° C. MS: m/e=456 (M+H$^+$).

Following the method of example 108 the compound of 109 was prepared.

EXAMPLE 109

2-[Methoxyacetyl-methyl-amino)-methyl]-N-(4-methoxy-7-morpholin-4-yl-benzothiazol-2-yl)-isonicotinamide Using methoxyacetyl chloride the title compound was prepared as yellow solid (73% yield), mp 210° C. MS: m/e=486 (M+H$^+$).

We claim:
1. A compound of the formula

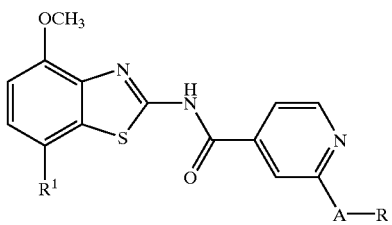

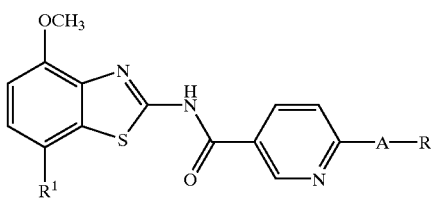

wherein
R¹ is phenyl, piperidin-1-yl or morpholinyl;
A is —O— and
R is —(CH₂)$_n$—N(R")—C(O)-lower alkyl, —(CH₂)$_n$—O-lower alkyl, —(CH₂)$_n$—O—(CH₂)$_n$—O-lower alkyl, lower alkyl, —(CH₂)$_n$-morpholinyl, —(CH₂)$_n$-phenyl, —(CH₂)$_n$—N(R")₂, —(CH₂)$_n$-pyridinyl, —(CH₂)$_n$—CF₃, —(CH₂)$_n$-2-oxo-pyrrolidinyl or C$_{4-6}$-cycloalkyl;
each R" is independently selected from hydrogen or lower alkyl; and
n is 1 or 2; or
A is —N(R')— and
R is lower alkyl, C$_{4-6}$-cycloalkyl, —(CH₂)$_n$—O-lower alkyl, —(CH₂)$_n$-pyridinyl, —(CH₂)$_n$-piperidinyl, —(CH₂)$_n$-phenyl, —(CH₂)$_n$—N(R")—C(O)-lower alkyl, —(CH₂)$_n$-morpholinyl, or —(CH₂)$_n$—N(R")₂;
R' and R" are independently selected from hydrogen or lower alkyl; and
n is 1 or 2; or
A is —CH₂— and
R is —N(R")—(CH₂)$_m$—O-lower alkyl, —N(R")₂, —S-lower alkyl or is acetidinyl, pyrrolidinyl or piperidinyl, which are optionally substituted by hydroxy or lower alkoxy or is morpholinyl, —N(R")—(CH₂)$_m$—C$_{4-6}$-cycloalkyl, —N(R")—(CH₂)$_m$—C(O)O-lower alkyl, —N(R")—(CH₂)$_m$—C(O)OH, -2-oxo-pyrrolidinyl, —N(R")—C(O)O-lower alkyl, —O(CH₂)$_m$—O-lower alkyl or alkoxy;
each R" is independently selected from hydrogen or lower alkyl; and
m is 1, 2 or 3;
or
A is —S— and
R is lower alkyl;
or
A—R are together p2 -piperazinyl, substituted by lower alkyl, —C(O)-lower alkyl or an oxo group, or is piperidinyl, substituted by lower alkoxy or hydroxy, or is morpholinyl, substituted by lower alkyl, or is —C$_{4-6}$-cycloalkyl, -azetidin-1-yl, optionally substituted by hydroxy or lower alkoxy, thiomorpholine-1,1-dioxo, -tetrahydopyran or 2-oxa-5-aza-bicyclo[2.2.1]hept-5-yl;
and pharmaceutically acceptable acid addition salts thereof.

2. The compound according to claim 1, wherein said compound has the formula IA.
3. The compound according to claim 2, wherein R¹ is morpholinyl.
4. The compound according to claim 3, wherein A is —O—.
5. The compound according to claim 4, wherein R is cycloalkyl, —(CH₂)$_n$—NHC(O)CH₃, —(CH₂)$_n$—N(R")₂, —(CH₂)$_n$—O-lower alkyl or lower alkyl.
6. The compound according to claim 5, wherein said compound is selected from the group consisting of:
2-(2-methoxy-ethoxy)-N-(4-methoxy-7-morpholin-4-yl-benzothiazol-2-yl)-isonicotinamide,
2-ethoxy-N-(4-methoxy-7-morpholin-4-yl-benzothiazol-2-yl)-isonicotinamide,
2-methoxy-N-(4-methoxy-7-morpholin-4-yl-benzothiazol-2-yl)-isonicotinamide,
2-isopropoxy-N-(4-methoxy-7-morpholin-4-yl-benzothiazol-2-yl)-isonicotinamide,
2-cyclohexyloxy-N-(4-methoxy-7-morpholin-4-yl-benzothiazol-2-yl)-isonicotinamide,
2-cyclopentyloxy-N-(4-methoxy-7-morpolin-4-yl-benzothiazol-2-yl)-isonicotinamide,
2-(2-dimethylamino-ethoxy)-N-(4-methoxy-7-morpholin-4-yl-benzothiazol-2-yl)-isonicotinamide and
2-(2-acetylamino-ethoxy)-N-(4-methoxy-7-morpholin-4-yl-benzothiazol-2-yl)-isonicotinamide.
7. The compound according to claim 4, wherein R is —(CH₂)$_n$-pyridinyl, —(CH₂)$_n$-morpholinyl- or —(CH₂)$_n$-2-oxo-pyrrolidinyl.
8. The compound according to claim 7, wherein said compound is selected from the group consisting of:
2-benzyloxy-N-(4-methoxy-7-morpholin-4-yl-benzothiazol-2-yl)-isonicotinamide,
N-(4-methoxy-7-morpholin-4-yl-benzothiazol-2-yl)-2-(pyridin-2-ylmethoxy)-isonicotinamide,
N-(4-methoxy-7-morpholin-4-yl-benzothiazol-2-yl)-2-[2-(2-oxo-pyrrolidin-1-yl)-ethoxy]-isonicotinamide and
N-(4-methoxy-7-morpholin-4-yl-benzothiazol-2-yl)-2-(2-morpholin-4-yl-ethoxy)-isonicotinamide.
9. The compound according to claim 3, wherein A is —N(R')—.
10. The compound according to claim 9, wherein R is —(CH₂)$_n$-pyridinyl, —(CH₂)$_n$-piperidinyl, —(CH₂)$_n$-phenyl or —(CH₂)$_n$-morpholidinyl.
11. The compound according to claim 10, wherein said compound is selected from the group consisting of:
N-(4-methoxy-7-morpholin-4-yl-benzothiazol-2-yl)-2-[methyl-(2-pyridin-2-yl-ethyl)-amino]-isonicotinamide,
N-(4-methoxy-7-morpholin-4-yl-benzothiazol-2-yl)-2-(2-pyridin-2-yl-ethylamino)-isonicotinamide,
N-(4-methoxy-7-morpholin-4-yl-benzothiazol-2-yl)-2-[(pyridin-2-ylmethyl)-amino]-isonicotinamide,
2-[ethyl-(2-pyridin-2-yl-ethyl)-amino]-N-(4-methoxy-7-morpholin-4-yl-benzothiazol-2-yl)-isonicotinamide,
N-(4-methoxy-7-morpholin-4-yl-benzothiazol-2-yl)-2-(2-morpholin-4-yl-ethylamino)-isonicotinamide,
N-(4-methoxy-7-morpholin-4-yl-benzothiazol-2-yl)-2-[methyl-(2-piperidin-1-yl-ethyl)-amino]-isonicotinamide,
N-(4-methoxy-7-morpholin-4-yl-benzothiazol-2-yl)-2-(2-piperidin-1-yl-ethylamino)-isonicotinamide, 2-benzylamino-N-(4-methoxy-7-morpholin-4-yl-benzothiazol-2-yl)-isonicotinamide, 2-(benzyl-methyl-amino)-N-(4-methoxy-7-morpholin-4-yl-benzothiazol-2-yl)-isonicotinamide, N-(4-methoxy-7-morpholin-4-yl-benzothiazol-2-yl)-2-(methyl-phenethyl-amino)-isonicotinamide and N-(4-methoxy-7-morpholin-4-yl-benzothiazol-2-yl)-2-phenethylamino-isonicotinamide.

12. The compound according, to claim 9, wherein R is lower alkyl, cycloalkyl, —(CH$_2$)$_n$—N(R")$_2$, —(CH$_2$)$_n$—O-lower alkyl or —(CH$_2$)$_n$—NR"—C(O)-lower alkyl.

13. The compound according to claim 12, wherein said compound is selected from the group consisting of:

2-[(2-methoxy-ethyl)-methyl-amino]-N-(4-methoxy-7-morpholin-4-yl-benzothiazol-2-yl)-isonicotinamide, 2-(2-methoxy-ethylamino)-N-(4-methoxy-7-morpholin-4-yl-benzothiazol-2-yl)-isonicotinamide, 2-[ethyl-(2-methoxy-ethyl)-amino]-N-(4-methoxy-7-morpholin-4-yl-benzothiazol-2-yl)-isonicotiniamide, 2-(2-ethoxy-ethylamino)-N-(4-methoxy-7-morpholin-4-yl-benzothiazol-2-yl)-isonicotinamide, 2-(2-acetylamino-ethylamino)-N-(4-methoxy-7-morpholin-4-yl-benzothiazol-2-yl)-isonicotinamide, 2-cyclohecylamino-N-(4-methoxy-7-mopholin-4-yl-benzothiazol-2-yl)-isonicotinamide, 2-cyclopentylamino-N-(4-methoxy-7-morpholin-4-yl-benzothiazol-2-yl)-isonicotinamide, 2-cyclobutylamino-N-(4-methoxy-7-morpholin-4-yl-benzothiazol-2-yl)-isonicotinamide, 2-(2-dimethylamino-ethylamino)-N-(4-methoxy-7-morpholin-4-yl-benzothiazol-2-yl)-isonicotinamide, N-(4-methoxy-7-morpholin-4-yl-benzothiazol-2-yl)-2-propylamino-isonicotinamide, N-(4-methoxy-7-morpholin-4-yl-benzothiazol-2-yl)-2-(methyl-propyl-amino)-isonicotinamide, 2-(cyclohexcyl-methyl-amino)-N-(4-methoxy-7-morpholin-4-yl-benzothiazol-2-yl)-isonicotinamide and 2-[(2-dimethylamino-ethyl)-methyl-amino]-N-(4-methoxy-7-morpholin-4-yl-benzothiazol-2-yl)-isonicotinamide.

14. The compound according to claim 3, wherein A is —CH$_2$—.

15. The compound according to claim 14, wherein R is —N(R")—(CH$_2$)$_m$—O-lower alkyl, —N(R")$_2$, —N(R")—(CH$_2$)$_m$-cycloalkyl, S-lower alkyl or -N(R")—(CH$_2$)$_m$—C(O)O-lower alkyl.

16. The compound according to claim 15, wherein said compound is selected from the group consisting of:

2-[(2-methoxy-ethylamino)-methyl]-N-(4-methoxy-7-morpholin-4-yl-benzothiazol-2-yl)-isonicotinamide, 2-[(2-ethoxy-ethylamino)-methyl]-N-(4-methoxy-7-morpholin-4-yl-benzothiazol-2-yl)-isonicotinamide, 2-[(butyl-methyl-amino)-methyl]-N-(4-methoxy-7-morpholin-4-yl-benzothiazol-2-yl)-isonicotinamide, 2-butylaminomethyl-N-(4-methoxy-7-morpholin-4-yl-benzothiazol-2-yl)-isonicotinamide, 2-diethylaminomethyl-N-(4-methoxy-7-morpholin-4-yl-benzothiazol-2-yl)-isonicotinamide, N-(4-methoxy-7-morpholin-4-yl-benzothiazol-2-yl)-2-methylaminomethyl-isonicotinamide, 2-ethylaminomethyl-N-(4-methoxy-7-morpholin-4-yl-benzothiazol-2-yl)-isonicotinamide, 2-[(cyclopropylmethyl-amino)-methyl]-N-(4-methoxy-7-morpholin-4-yl-benzothiazol-2-yl)-isonicotinamide, 4-{[4-(4-methoxy-7-morpholin-4-yl-benzothiazol-2-yl-carbamoyl)-pyridin-2-yl-methyl]-amino}-butyric acid tert-butyl ester,

[4-(4-methoxy-7-morpholin-4-yl-benzothiazol-2-yl-carbamoyl)-pyridin-2-ylmethyl]-methyl-carbamic acid methyl ester, 2-ethylsulfanylmethyl-N-(4-methoxy-7-morpholin-4-yl-benzothiazol-2-yl)-isonicotinamide, 2-{[(2-ethoxy-ethyl)-methyl-amino]-methyl}-N-(4-methoxy-7-morpholin-4-yl-benzothiazol-2-yl)-isonicotinamide, 2-Ethylsulfanylmethyl-N-(4-methoxy-7-morpholin-4-yl-benzothiazol-2-yl)-isonicotinamide, and 2-{[(2-Ethoxy-ethyl)-methyl-amino]-methyl}-N-(4-methoxy-7-morpholin-4-yl-benzothiazol-2-yl)-isonicotinamide.

17. The compound according to claim 14, wherein R is substituted or unsubstituted pyrrolidinyl, substituted or unsubstituted -2-oxo-pyrrolidinyl, substituted or unsubstituted piperidinyl, morpholinyl, or alkoxy, wherein, when R is substituted, the substituted is lower alkoxy or hydroxy.

18. The compound according to claim 17, wherein said compound is selected from the group consisting of:

N-(4-methoxy-7-morpholin-4-yl-benzothiazol-2-yl)-2-pyrrolidin-1-ylmethyl-isonicotinamide, N-(4-methoxy-7-morpholin-4-yl-benzothiazol-2-yl)-2-(2-oxo-pyrrolidin-1-yl-methyl)-isonicotinamide, N-(4-methoxy-7-morpholin-4-yl-benzothiazol-2-yl)-2-(4-methoxy-piperidin-1-ylmethyl)-isonicotinamide, N-(4-methoxy-7-morpholin-4-yl-benzothiazol-2-yl)-2-piperidin-1-ylmethyl-isonicotinamide, 2-(4-hydroxy-piperidin-1-ylmethyl)-N-(4-methoxy-7-morpholin-4-yl-benzothiazol-2-yl)-isonicotinamide, N-(4-methoxy-7-morpholin-4-yl-benzothiazol-2-yl)-2-morpholin-4-ylmethyl-isonicotinamide, 2-methoxymethyl-N-(4-methoxy-7-morpholin-4-yl-benzothiazol-2-yl)-isonicotinamide and 2-(4-hydroxy-piperidin-1-yl-methyl)-N-(4-methoxy-7-morpholin-4-yl-benzothiazol-2-yl)-isonicotinamide.

19. The compound according to claim 3, wherein A is —S—.

20. The compound according to claim 19, wherein said compound is selected from the group consisting of:

N-(4-methoxy-7-morpholin-4-yl-benzothiazol-2-yl)-2-methylsulfanyl-isonicotinamide and 2-ethylsulfanyl-N-(4-methoxy-7-morpholin-4-yl-benzothiazol-2-yl)-isonicotinamide.

21. The compound according to claim 3, wherein A—R are together -piperazinyl, substituted by lower alkyl, —C(O)-lower alkyl or an oxo group, or is piperidinyl, substituted by lower alkoxy or hydroxy, or is morpholinyl, substituted by lower alkyl, or is -cyclohexyl, -azetidin-1-yl, which is optionally substituted by hydroxy or lower alkoxy, or is -tetrahydopyran, or is 1,1-dioxo-thiomorpholinyl or 2-oxa-5-aza-bicyclo[2.2.1]hept-5-yl.

22. The compound according to claim 21, wherein said compound is selected from the group consisting of:

N-(4-methoxy-7-morpholin-4-yl-benzothiazol-2-yl)-2-(4-methyl-piperazin-1-yl)-isonicotinamide, 2-(4-acetyl-piperazin-1-yl)-N-(4-methoxy-7-morpholin-4-yl-benzothiazol-2-yl)-isonicotinamide, N-(4-methoxy-7-morpholin-4-yl-benzothiazol-2-yl)-2-(4-methyl-3-oxo-piperazin-1-yl)-isonicotinamide, 2-(4-ethyl-3-oxo-piperazin-1-yl)-N-(4-methoxy-7-morpholin-4-yl-benzothiazol-2-yl)-isonicotinamide, 2-[(2R,6S)-2,6-dimethyl-morpholin-4-yl]-N-(4-methoxy-7-morpholin-4-yl-benzothiazol-2-isonicotinamide, 2-cyclohexyl-N-(4-methoxy-7-morpholin-4-yl-benzothiazol-2-yl)-isonicotinamide, 2-azetidin-1-yl-N-(4-methoxy-7-morpholin-4-yl-benzothiazol-2-yl)-isonicotinamide, N-(4-methoxy-7-morpholin-4-yl-benzothiazol-2-yl)-2-(4-methoxy-piperidin-1-yl)-isonicotinamide, N-(4-methoxy-7-morpholin-4-yl-benzothiazol-2-yl)-2-(3-methoxy-piperidin-1-yl)-isonicotinamide, 2-(3-hydroxy-piperidin-1-yl)-N-(4-Methoxy-7-morpholin-4-yl-benzothiazol-2-yl)-isonicotinamide, N-(4-methoxy-7-morpholin-4-yl-benzothiazol-2-yl)-2-(tetrahydro-pyran-4-yl)-isonicotinamide, N-(4-methoxy-7-morpholin-4-yl-benzothiazol-2-yl)-2-{(1S,4S)-2-oxa-5-aza-bicyclo[2.2.1]hept-5-yl}-isonicotinamide, 2-(1,1-dioxo-1l6-thiomorpholin-4-yl)-N-(4-methoxy-7-morpholin-4-yl-benzothiazol-2-yl)-isonicotinamide, 2-(3-hydroxy-azetidin-1-yl)-N-(4-methoxy-7-morpholin-4-yl-benzothiazol-2-yl)-isonicotinamide, 2-(3-methoxy-azetidin-1-yl)-N-(4-methoxy-7-morpholin-4-yl-benzothiazol-2-yl)-isonicotinamide and 2-(3-ethoxy-azetidin-1-yl)-N-(4-methoxy-7-morpholin-4-yl-benzothiazol-2-yl)-isonicotinamide.

23. The compound according to claim 2, wherein $R^1$ is piperidinyl.

24. The compound according to claim 23, wherein A is —$CH_2$— and R is pyrrolidinyl or morpholidinyl.

25. The compound according to claim 24, wherein the compound is selected from the group consisting of:

N-(4-methoxy-7-piperidin-1-yl-benzothiazol-2-yl)-2-pyrrolidin-1-yl-methyl-isonicotinamide and N-(4-methoxy-7-piperidin-1-yl-benzothiazol-2-yl)-2-morpholin-4-yl-methyl-isonicotinamide.

26. The compound according to claim 1, wherein said compound has the formula IB.

27. The compound according to claim 26, wherein $R^1$ is morpholinyl.

28. The compound according to claim 27, wherein A is —O— and R is lower alkyl, —$(CH_2)_2$—O-lower alkyl or cycloalkyl.

29. The compound according to claim 28, wherein said compound is selected from the group consisting of:

6-methoxy-N-(4-methoxy-7-morpholin-4-yl-benzothiazol-2-yl)-nicotinamide, 6-isopropoxy-N-(4-methoxy-7-morpholin-4-yl-benzothiazol-2-yl)-nicotinamide, 6-(2-methoxy-ethoxy)-N-(4-methoxy-7-morpholin-4-yl-benzothiazol-2-yl)-nicotinamide and 6-cyclohexyloxy-N-(4-methoxy-7-morpholin-4-yl-benzothiazol-2-yl)-nicotinamide.

30. The compound according to claim 23, wherein A—R are together piperazinyl, substituted by lower alkyl.

31. The compound according to claim 30, wherein said compound is

N-(4-methoxy-7-piperidin-1-yl-benzothiazol-2-yl)-2-(4-methyl-piperazin-1-yl)-isonicotinamide.

32. The compound according to claim 2, wherein $R^1$ is phenyl, A is —O— and R is lower alkyl.

33. The compound according to claim 32, wherein said compound is 2-methoxy-N-(4-methoxy-7-phenyl-benzothiazol-2-yl)-isonicotinamide.

34. A process for preparing a compound of formula IA or IB as defined in claim 1, which processes comprises:

reacting a compound of formula

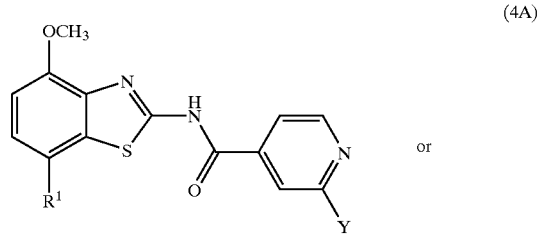

(4A)

or

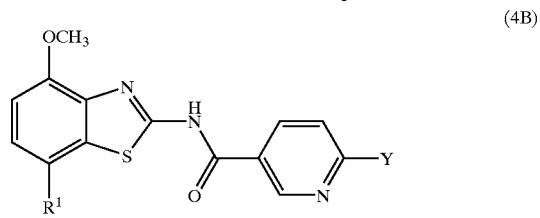

(4B)

with a Compound of formula

(5)

in the presence of a base to yield a compound of formula

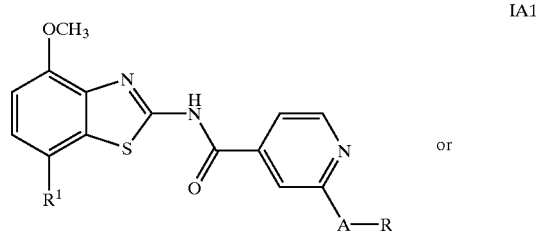

IA1 or

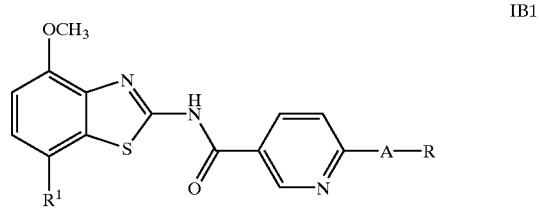

IB1 wherein R is —$(CH_2)_n$—N(R")—C(O)-lower alkyl, —$(CH_2)_n$—O-lower alkyl, —$(CH_2)_n$—O—$(CH_2)_n$—O-lower alkyl, lower alkyl, —$(CH_2)_n$-morpholinyl, —$(CH)_n$-phenyl, —$(CH_2)_n$—N(R")$_2$, —$(CH_2)_n$-pyridinyl, -$(CH_2)_n$—$CF_3$, —$(CH_2)_n$-2-oxo-pyrrolidinyl or $C_{4-6}$-cycloalkyl, Y is chloro or bromo, A is oxygen or sulfur, and n is 1 or 2.

35. A process for preparing a compound of formula IA or IB as defined in claim 1, which processes comprises:

reacting a compound of formula

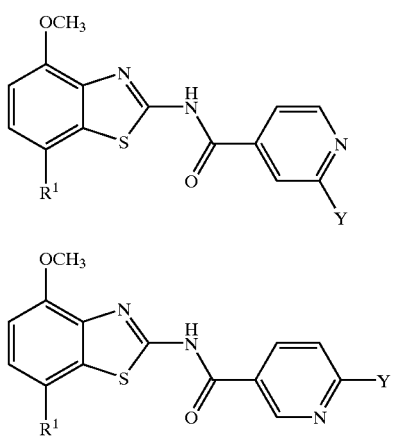

(4A)

or (4B)

with a compound of formula

HNRR'  (6)

to yield a compound of formula

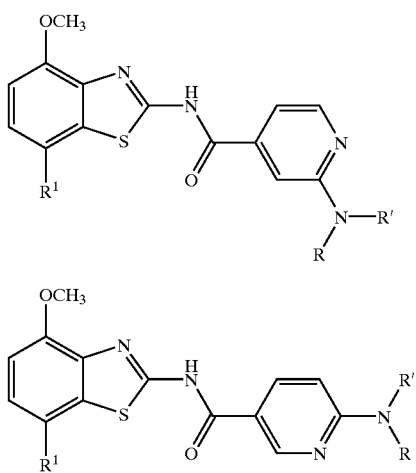

IA2 or

IB2 wherein R is lower alkyl, $C_{4-6}$-cycloalkyl, —$(CH_2)_n$—O-lower alkyl, —$(CH_2)_n$-pyridinyl, —$(CH_2)_n$-piperidinyl, —$(CH_2)_n$-phenyl, —$(CH_2)_n$—N(R")—C(O)-lower alkyl, —$(CH_2)_n$-morpholinyl or —$(CH)_n$—N(R")$_2$ or R and R' form together with the N atom the following groups: piperazinyl, optionally substituted by lower alkyl, C(O)-lower alkyl or an oxo group, piperidinyl, optionally substituted by lower alkoxy or hydroxy, morpholinyl, morpholinyl substituted by lower alkyl, azetidin-1-yl, azetidin-1-yl substituted by hydroxy or lower alkoxy, or thiomorpholine-1,1-dioxo or 2-oxa-bicyclo[2.21]hept-5-yl, R' and R" are independently selected from hydrogen or lower alkyl, Y is chloro or bromo and n is 1 or 2.

36. A process for preparing, a compound of formula IA or IB as defined in claim 1, which processes comprises:

reacting, a compound of formula

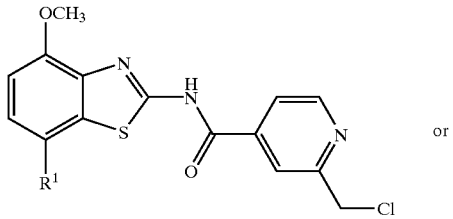

4A1 or

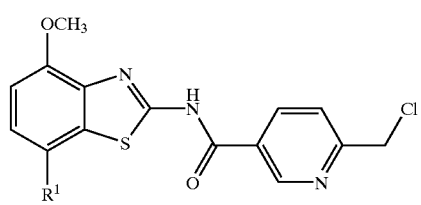

4B1 with a compound of formula

H—R  (9)

to yield a compound of formula

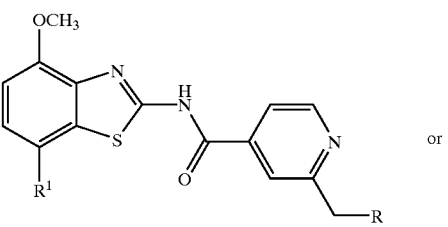

IA3-1 or

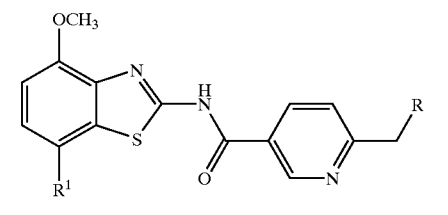

IB3-1 wherein R is —N(R")—$(CH_2)_m$-lower alkyl, —N(R")$_2$, —S-lower alkyl or is substituted or unsubstituted acetidinyl, substituted or unsubstituted pyrrolidinyl, substituted or unsubstituted piperidinyl, morpholinyl, —N(R")—$(CH_2)_m$—$C_{4-6}$-cycloalkyl, N(R")—$(CH_2)_m$—C(O)O-lower alkyl, —N(R")—$(CH_2)_m$—C(O)OH, -2-oxo-pyrrolidinyl, —N(R")—C(O)O-lower alkyl, or —O$(CH_2)_m$—O-lower alkyl or alkoxy, wherein when R is substituted, the substituent is hydroxy or lower alkoxy;

R" is independently from each other hydrogen or lower alkyl; and m is 1, 2 or 3.

37. A process for preparing a compound of formula IA or IB as defined in claim 1, which processes comprises:

reacting a compound of formula

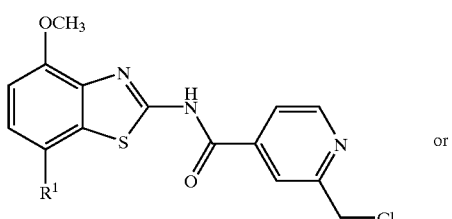  (4A1)

or

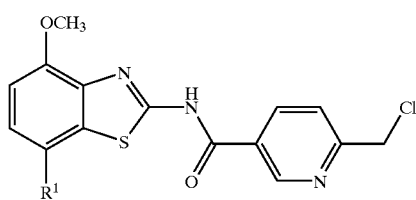  (4B1)

with a compound of formula

H—O—R  (5)

to give yield a compound of formula

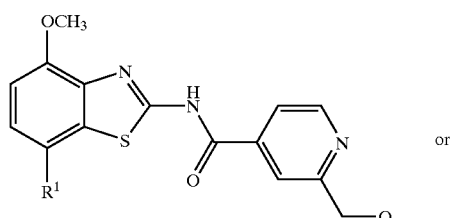  IA3-2 or

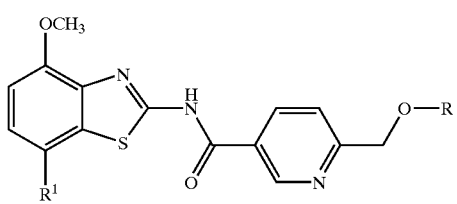  IB3-2 wherein R is —(CH$_2$)$_n$—O-lower alkyl or is lower alkyl; and m is 1, 2 or 3.

38. A process for preparing a compound of formula IA or IB as defined in claim 1, which processes comprises:

reacting a compound of formula

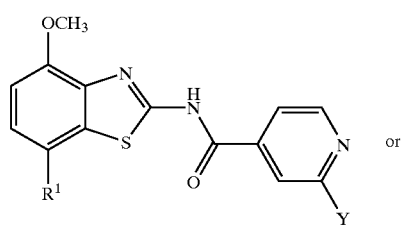  (4A)

or

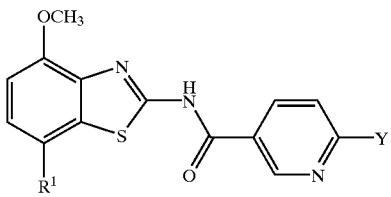  (4B)

with a compound of formula

Bu$_3$Sn—A'—R/cat or with B(OH)$_2$—A'—R/cat to yield a compound of formula

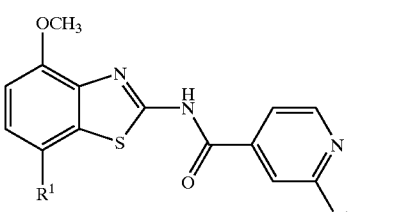  IA4 or

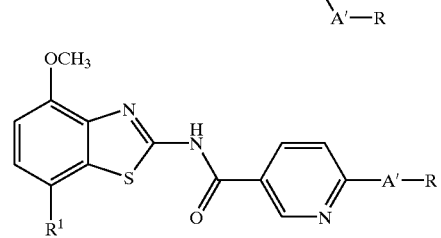  IB4 wherein A'—R are together C$_{4-6}$-cycloalkenyl or dihydopyran and Y is bromo;

reacting a compound of formula IA4 or IB4 with hydrogen and a catalyst to give a compound of formula

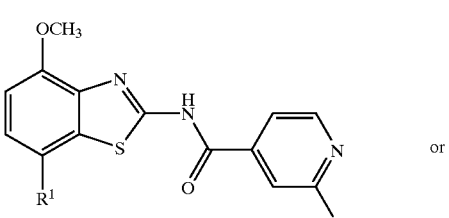  IA5 or

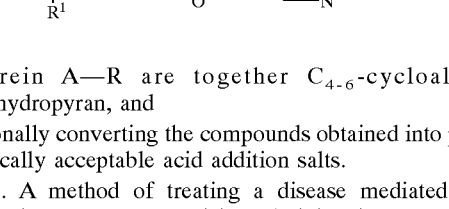  IB5 wherein A—R are together C$_{4-6}$-cycloalkyl or tetrahydropyran, and optionally converting the compounds obtained into pharmaceutically acceptable acid addition salts.

39. A method of treating a disease mediated by the adenosine receptor comprising administering to a patient in need of such treatment, an effective amount of a compound selected from the formulas IA and IB

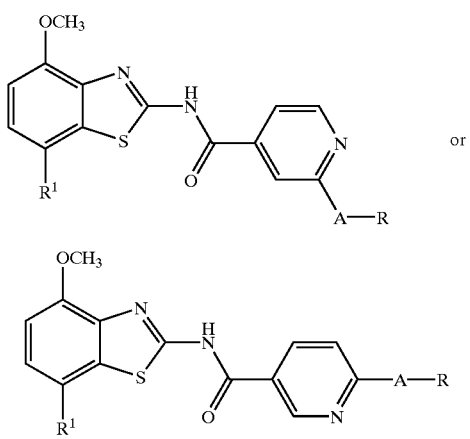

wherein
- $R^1$ is phenyl, piperidin-1-yl or morpholinyl;
- A is —O— and
- R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl, —(CH$_2$)$_n$—N(R")$_2$, —(CH$_2$)$_n$-pyridinyl, —(CH$_2$)$_n$—CF$_3$, —(CH$_2$)$_n$-2-oxo-pyrrolidinyl or C$_{4-6}$-cycloalkyl;
   - each R" is independently selected from hydrogen or lower alkyl; and
   - n is 1 or 2; or
- A is —N(R')— and
- R is lower alkyl, C$_{4-6}$-cycloalkyl, —(CH$_2$)$_n$—O-lower alkyl, —(CH$_2$)$_n$-pyridinyl, —(CH$_2$)$_n$-piperidinyl, —(CH$_2$)$_n$-phenyl, —(CH$_2$)$_n$—N(R")—C(O)-lower alkyl, —(CH$_2$)$_n$-morpholinyl, or —(CH$_2$)$_n$—N(R")$_2$;
   - R' and R" are independently selected from hydrogen or lower alkyl; and
   - n is 1 or 2; or
- A is —CH$_2$— and
- R is —N(R")—(CH$_2$)$_m$—O-lower alkyl, —N(R")$_2$, —S-lower alkyl or is acetidinyl, pyrrolidinyl or piperidinyl, which are optionally substituted by hydroxy or lower alkoxy or is morpholinyl, —N(R")—(CH$_2$)$_m$—C$_{4-6}$-cycloalkyl, —N(R")—(CH$_2$)$_m$—C(O)O-lower alkyl, —N(R")—(CH$_2$)$_m$—C(O)OH, -2-oxo-pyrrolidinyl, —N(R")—C(O)O-lower alkyl, —O(CH$_2$)$_m$—O-lower alkyl or alkoxy;
   - each R" is independently selected from hydrogen or lower alkyl; and
   - m is 1, 2 or 3;
or
- A is —S— and
- R is lower alkyl;
or
- A—R are together
   - -piperazinyl, substituted by lower alkyl, —C(O)-lower alkyl or an oxo group, or is piperidinyl, substituted by lower alkoxy or hydroxy, or is morpholinyl, substituted by lower alkyl, or is —C$_{4-6}$-cycloalkyl, -azetidin-1-yl, optionally substituted by hydroxy or lower alkoxy, thiomorpholine-1,1-dioxo, -tetrahydopyran or 2-oxa-5-aza-bicyclo[2.2.1]hept-5-yl;

and pharmaceutically acceptable acid addition salts thereof.

40. The method according to claim 39, wherein said disease is selected from at least one of Alzheimer's disease, Parkinson's disease, Huntington's disease, neuroprotection, schizophrenia, anxiety, pain, respiration deficits, depression, drug addiction, asthma, allergic responses, hypoxia, ischaemia, seizure, and attention deficit hyperactivity disorder.

41. The method according to claim 39, wherein said adenosine receptor is the A$_{2A}$ receptor.

42. The method according to claim 41, wherein said disease is selected from the group consisting of Alzheimer's disease, depression, drug addiction, neuroprotection, Parkinson's disease, and attention deficit hyperactivity disorder.

43. A pharmaceutical composition comprising a pharmaceutically effective amount of a compound selected from the formulas IA and IB

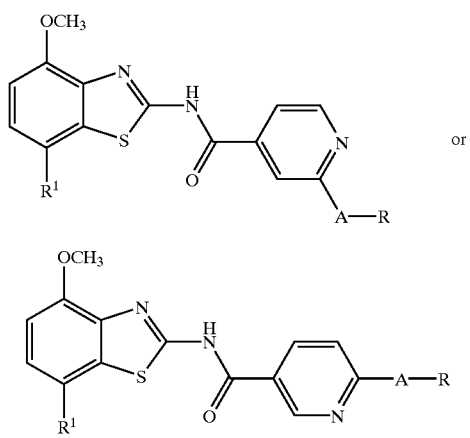

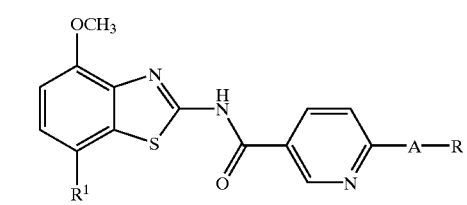

wherein
- $R^1$ is phenyl, piperidin-1-yl or morpholinyl;
- A is —O— and
- R is —(CH$_2$)$_n$—N(R")—C(O)-lower alkyl, —(CH$_2$)$_n$—O-lower alkyl, —(CH$_2$)$_n$—O—(CH$_2$)$_n$—O-lower alkyl, lower alkyl, —(CH$_2$)$_n$-morpholinyl, —(CH$_2$)$_n$-phenyl, —(CH$_2$)$_n$—N(R")$_2$, —(CH$_2$)$_n$-pyridinyl, —(CH$_2$)$_n$—CF$_3$, —(CH$_2$)$_n$-2-oxo-pyrrolidinyl or C$_{4-6}$-cycloalkyl;
   - each R" is independently selected from hydrogen or lower alkyl; and
   - n is 1 or 2; or
- A is —N(R')— and
- R is lower alkyl, C$_{4-6}$-cycloalkyl, —(CH$_2$)$_n$—O-lower alkyl, —(CH$_2$)$_n$-pyridinyl, —(CH$_2$)$_n$-piperidinyl, —(CH$_2$)$_n$-phenyl, —(CH$_2$)$_n$—N(R")—C(O)-lower alkyl, —(CH$_2$)$_n$-morpholinyl, or —(CH$_2$)$_n$—N(R")$_2$;
   - R' and R" are independently selected from hydrogen or lower alkyl; and
   - n is 1 or 2; or
- A is —CH$_2$— and
- R is —N(R")—(CH$_2$)$_m$—O-lower alkyl, —N(R")$_2$, —S-lower alkyl or is acetidinyl, pyrrolidinyl or piperidinyl, which are optionally substituted by hydroxy or lower alkoxy or is morpholinyl, —N(R")—(CH$_2$)$_m$—C$_{4-6}$-cycloalkyl, —N(R")—(CH$_2$)$_m$—C(O)O-lower alkyl, —N(R")—(CH$_2$)$_m$—C(O)OH, -2-oxo-pyrrolidinyl, —N(R")—C(O)O-lower alkyl, —O(CH$_2$)$_n$—O-lower alkyl or alkoxy;

each R" is independently selected from hydrogen or lower alkyl; and m is 1, 2 or 3;

or

A is —S— and

R is lower alkyl;

or

A—R are together

-piperazinyl, substituted by lower alkyl, —C(O)-lower alkyl or an oxo group, or is piperidinyl, substituted by lower alkoxy or hydroxy, or is morpholinyl, substituted by lower alkyl, or is —$C_{4-6}$-cycloalkyl, -azetidin-1-yl, optionally substituted by hydroxy or lower alkoxy, thiomorpholine-1,1-dioxo, -tetrahydopyran or 2-oxa-5-aza-bicyclo[2.2.1]hept-5-yl;

and pharmaceutically acceptable acid addition salts thereof; and a pharmaceutically acceptable carrier.

* * * * *

UNITED STATES PATENT AND TRADEMARK OFFICE
CERTIFICATE OF CORRECTION

PATENT NO. : 6,620,811 B2
DATED : September 16, 2003
INVENTOR(S) : Alexander Flohr et al.

It is certified that error appears in the above-identified patent and that said Letters Patent is hereby corrected as shown below:

<u>Column 47,</u>
Line 59, replace "A-R are together p2 –piperazinyl, substituted by lower" with
-- A-R are together –piperazinyl, substituted by lower --.

Signed and Sealed this

Thirtieth Day of December, 2003

JAMES E. ROGAN
*Director of the United States Patent and Trademark Office*